United States Patent
Wang et al.

(10) Patent No.: US 12,139,523 B2
(45) Date of Patent: Nov. 12, 2024

(54) ANTI-LMP2 TCR-T CELL THERAPY FOR THE TREATMENT OF EBV-ASSOCIATED CANCERS

(71) Applicant: DUKE UNIVERSITY, Durham, NC (US)

(72) Inventors: Xiao-Fan Wang, Durham, NC (US); Peter Alexander, Durham, NC (US); Qi-Jing Li, Durham, NC (US); Guoping Wang, Durham, NC (US)

(73) Assignee: Duke University, Durham, NC (US)

( * ) Notice: Subject to any disclaimer, the term of this patent is extended or adjusted under 35 U.S.C. 154(b) by 682 days.

(21) Appl. No.: 17/276,553

(22) PCT Filed: Nov. 26, 2019

(86) PCT No.: PCT/US2019/063310
§ 371 (c)(1),
(2) Date: Mar. 16, 2021

(87) PCT Pub. No.: WO2020/112815
PCT Pub. Date: Jun. 4, 2020

(65) Prior Publication Data
US 2022/0056101 A1 Feb. 24, 2022

Related U.S. Application Data

(60) Provisional application No. 62/771,653, filed on Nov. 27, 2018.

(51) Int. Cl.
*C07K 14/725* (2006.01)
*A61K 35/17* (2015.01)
*A61P 35/00* (2006.01)
*C07K 16/08* (2006.01)

(52) U.S. Cl.
CPC .......... *C07K 14/7051* (2013.01); *A61K 35/17* (2013.01); *A61P 35/00* (2018.01); *C07K 16/085* (2013.01)

(58) Field of Classification Search
CPC .. C07K 14/7051; C07K 16/085; A61K 35/17; A61K 2239/48; A61K 39/4611; A61K 39/4632; A61K 39/464838; A61K 38/00; A61K 2239/31; A61K 2239/38; A61K 2239/46; A61P 35/00; C12N 2501/22; C12N 2501/2302; C12N 2501/24; C12N 5/0636; C12N 2501/25; C12N 2510/00; C12N 2501/51; C12N 2501/515; C12N 2501/998
See application file for complete search history.

(56) References Cited

U.S. PATENT DOCUMENTS

| | | |
|---|---|---|
| 2013/0052733 A1 | 2/2013 | Chang |
| 2018/0230193 A1 | 8/2018 | Loew et al. |

FOREIGN PATENT DOCUMENTS

| | | |
|---|---|---|
| CN | 102695717 A | 9/2012 |
| CN | 106632659 A | 5/2017 |
| CN | 107001444 A | 8/2017 |
| WO | 2015022520 A1 | 2/2015 |
| WO | WO 2016/095783 A1 | 6/2016 |
| WO | WO2017085471 A1 | 5/2017 |
| WO | WO2017109496 A1 | 6/2017 |
| WO | 2018/067618 A1 | 4/2018 |
| WO | 2018/144535 A1 | 8/2018 |

OTHER PUBLICATIONS

Van Regenmortel. From absolute to exquisite specificity. Reflections on the fuzzy nature of species, specificity and antigenic sites. J Immunol Methods. 1998; 216(1-2):37-48. (Year: 1998).*
Frank SA. Immunology and Evolution of Infectious Disease. Princeton (NJ): Princeton University Press; 2002. Chapter 4, Specificity and Cross-Reactivity. (Year: 2002).*
Zheng, Y. et al. (2015) Human Leukocyte Antigen (HLA) A*1101-Restricted Epstein-Barr Virus-Specific T-cell Receptor Gene Transfer to Target Nasopharyngeal Carcinoma. Cancer Immunology Research. 3(10): 1138-1147.
Bollard, CM, et al. (2004) Cytotoxic T Lymphocyte Therapy for Epstein-Barr Virus+ Hodgkin's Disease, J Exp Med, 200 (12):1623-1633.
Bollard, CM, et al. (2004) The Generation and Characterization of LMP2-Specific CTLs for Use as Adoptive Transfer From Patients With Relapsed EBV-Positive Hodgkin Disease, J. of Immunotherapy, 27(4):317-327.
Pauline Meij et al., "Identification and prevalence of CD8+ T-cell responses directed against Epstein-Barr virus-encoded latent membrane protein 1 and latent membrane protein 2", International Journal of Cancer, Mar. 27, 2002, vol. 99, No. 1, p. 93-99.

* cited by examiner

*Primary Examiner* — Brad Duffy
*Assistant Examiner* — Amber K Faust
(74) *Attorney, Agent, or Firm* — POLSINELLI PC

(57) ABSTRACT

The present disclosure provides compositions comprising anti-LMP2 TCR-T cell populations for the treatment of EBV-associated cancers and methods of making and using same.

19 Claims, 14 Drawing Sheets
Specification includes a Sequence Listing.

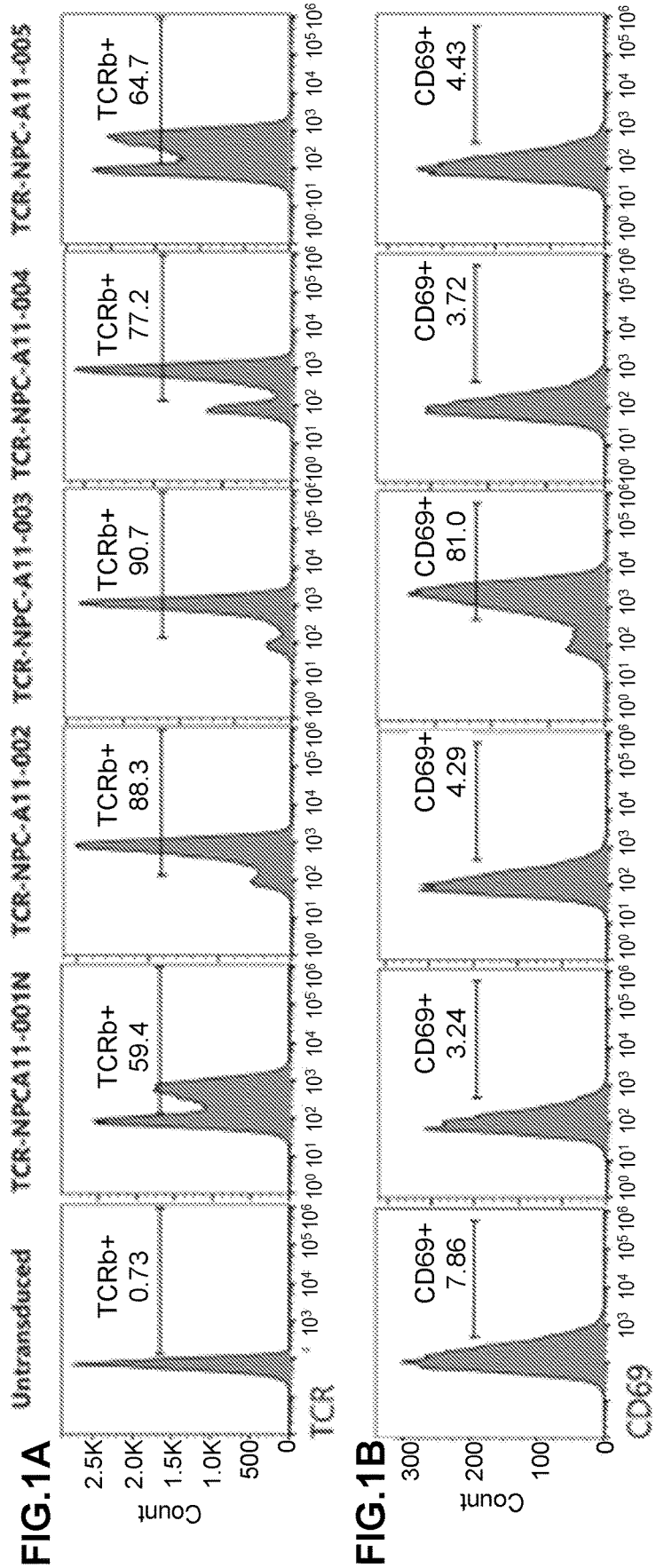

FIG.5 - continued
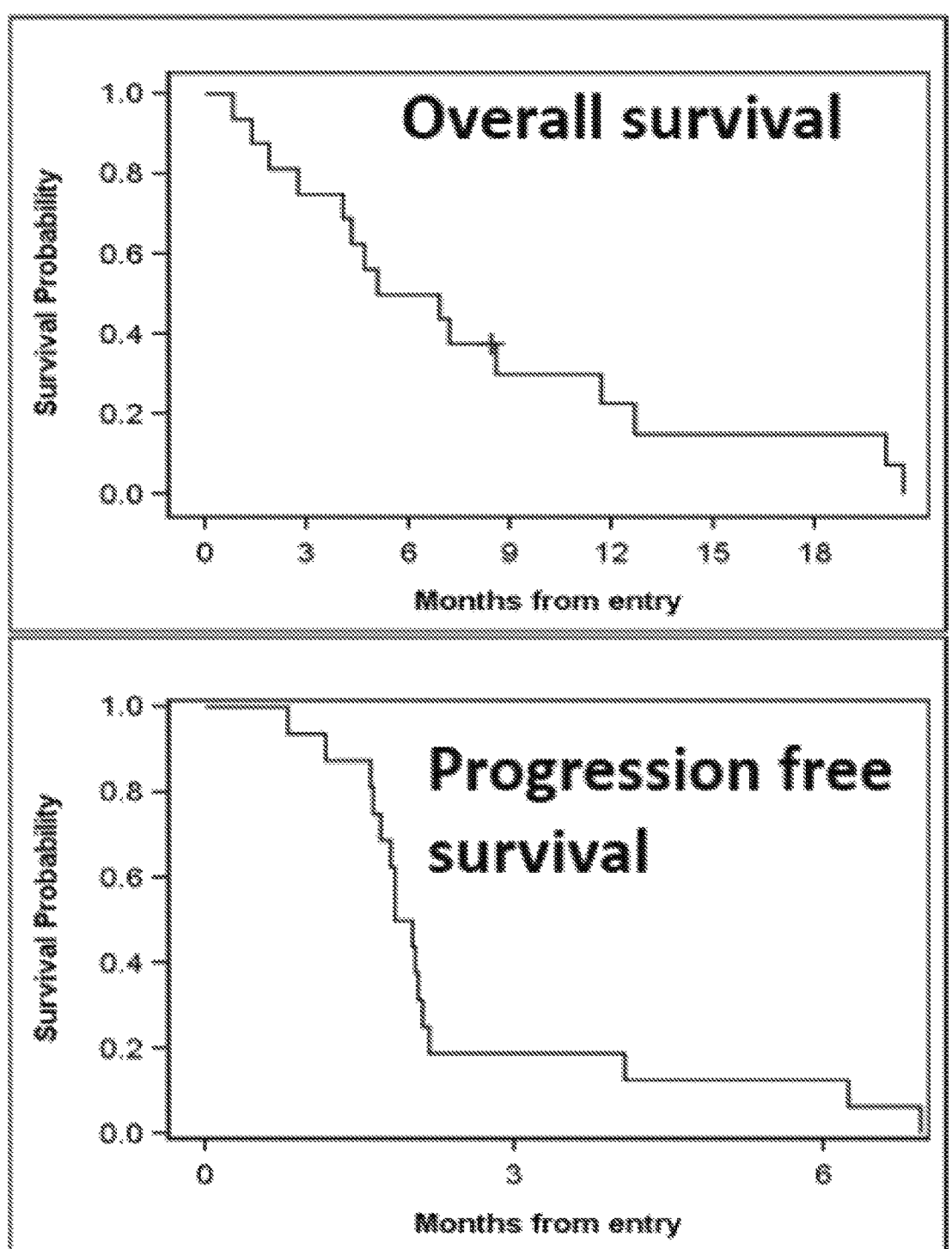

FIG.5 - continued
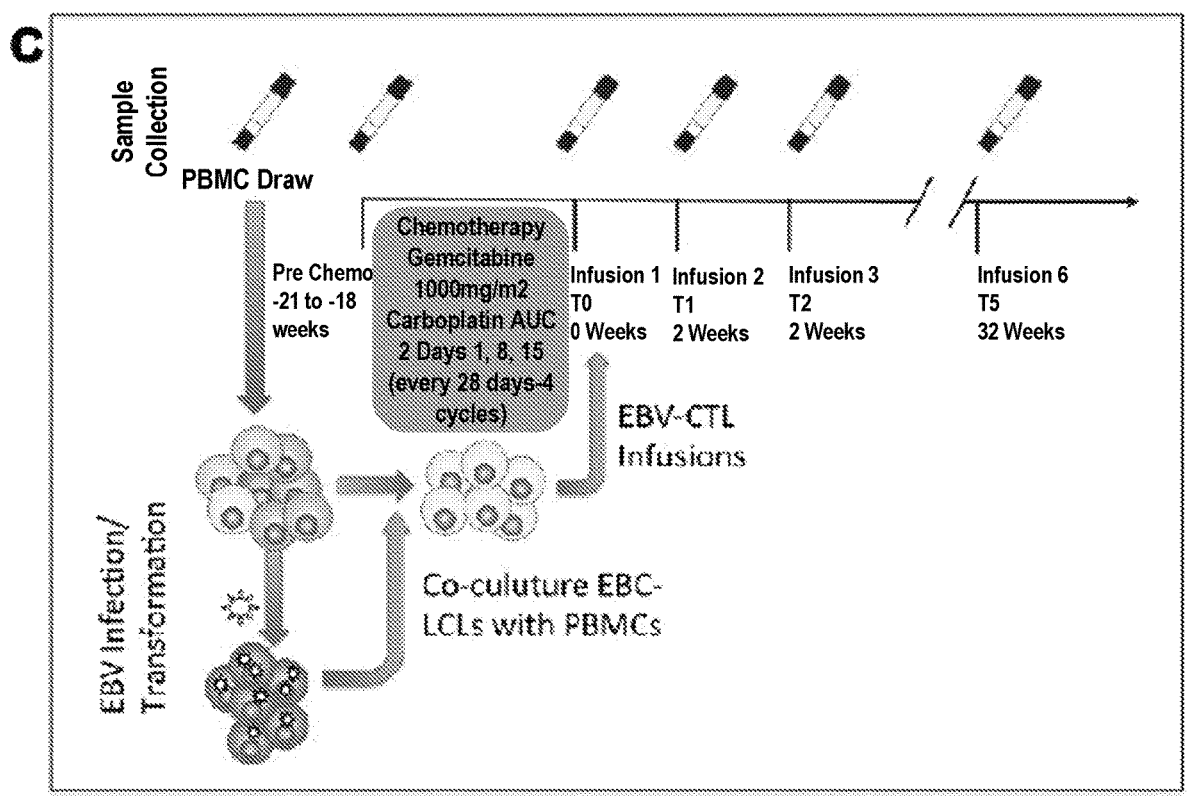

FIG.5 - continued
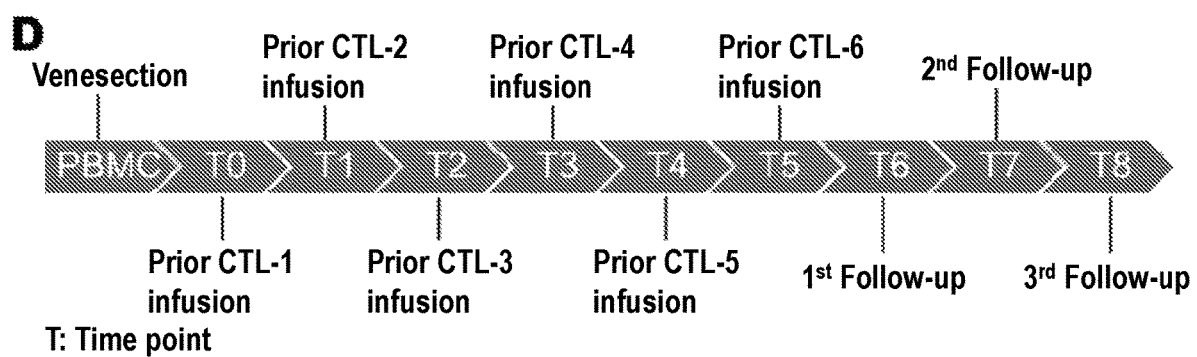

FIG.5 - continued
E
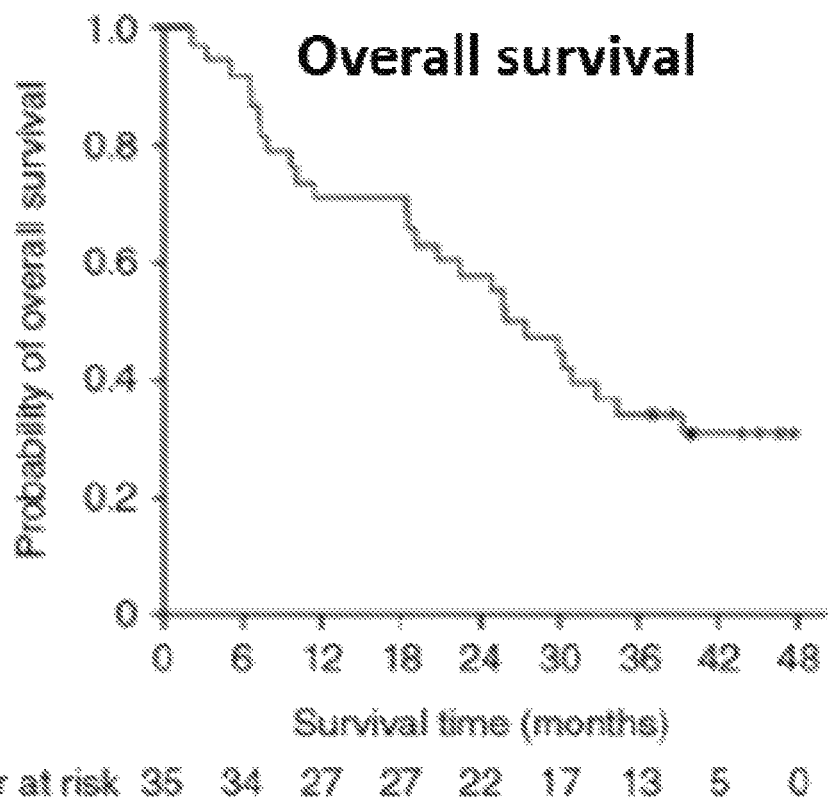
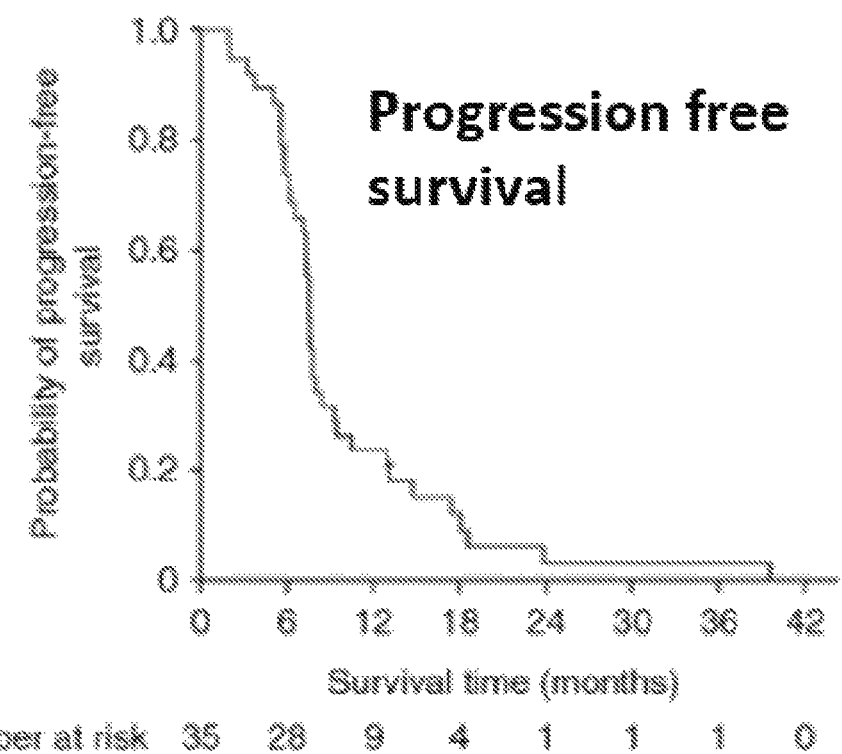

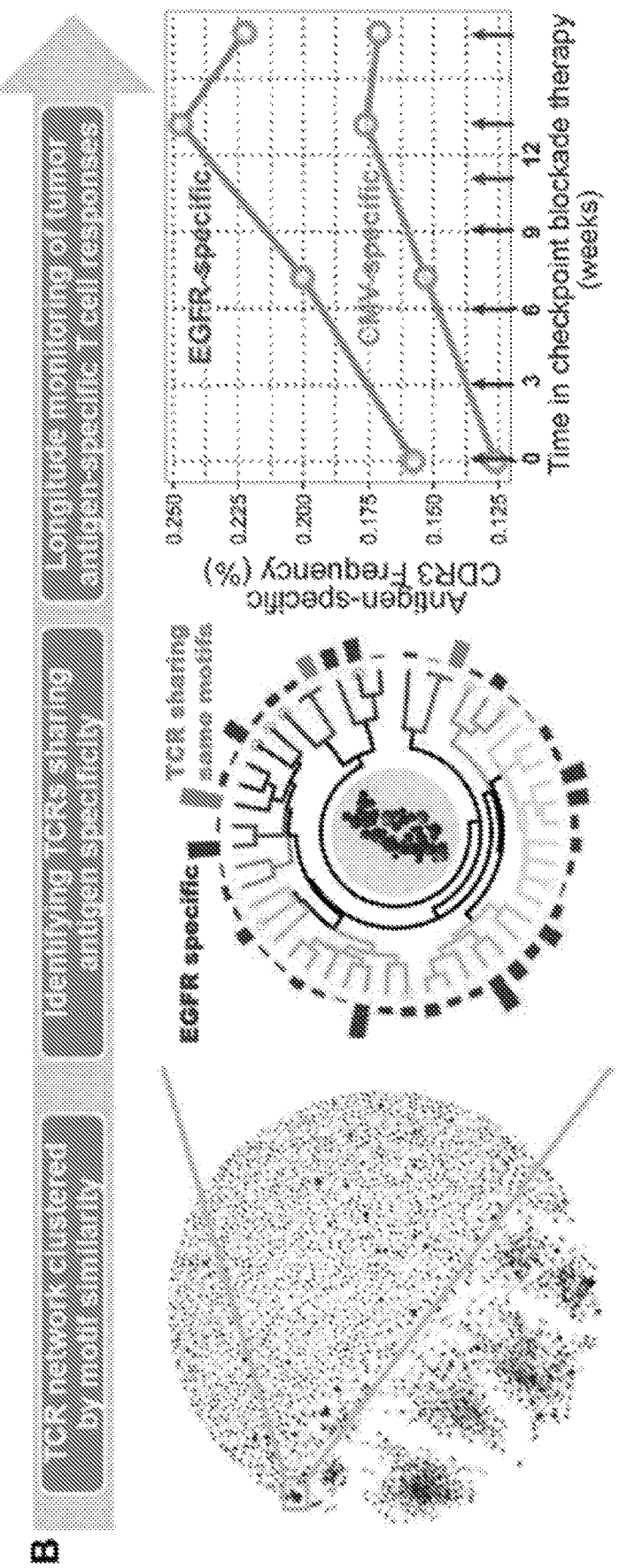
FIG.6 - continued

FIG.7
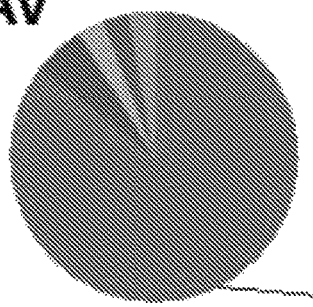
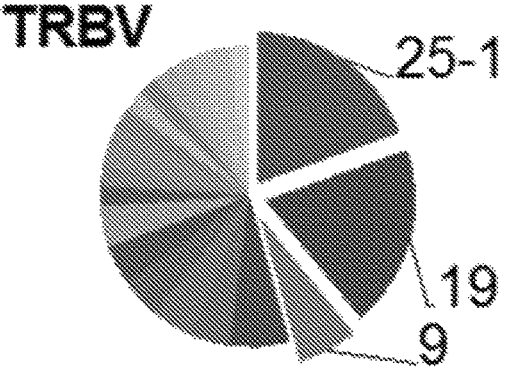
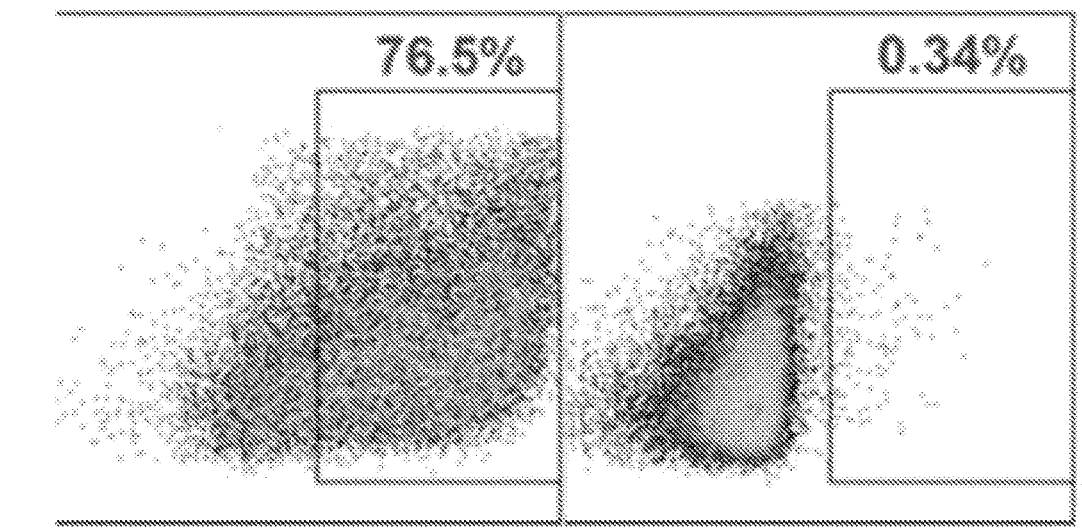

FIG.7 - continued
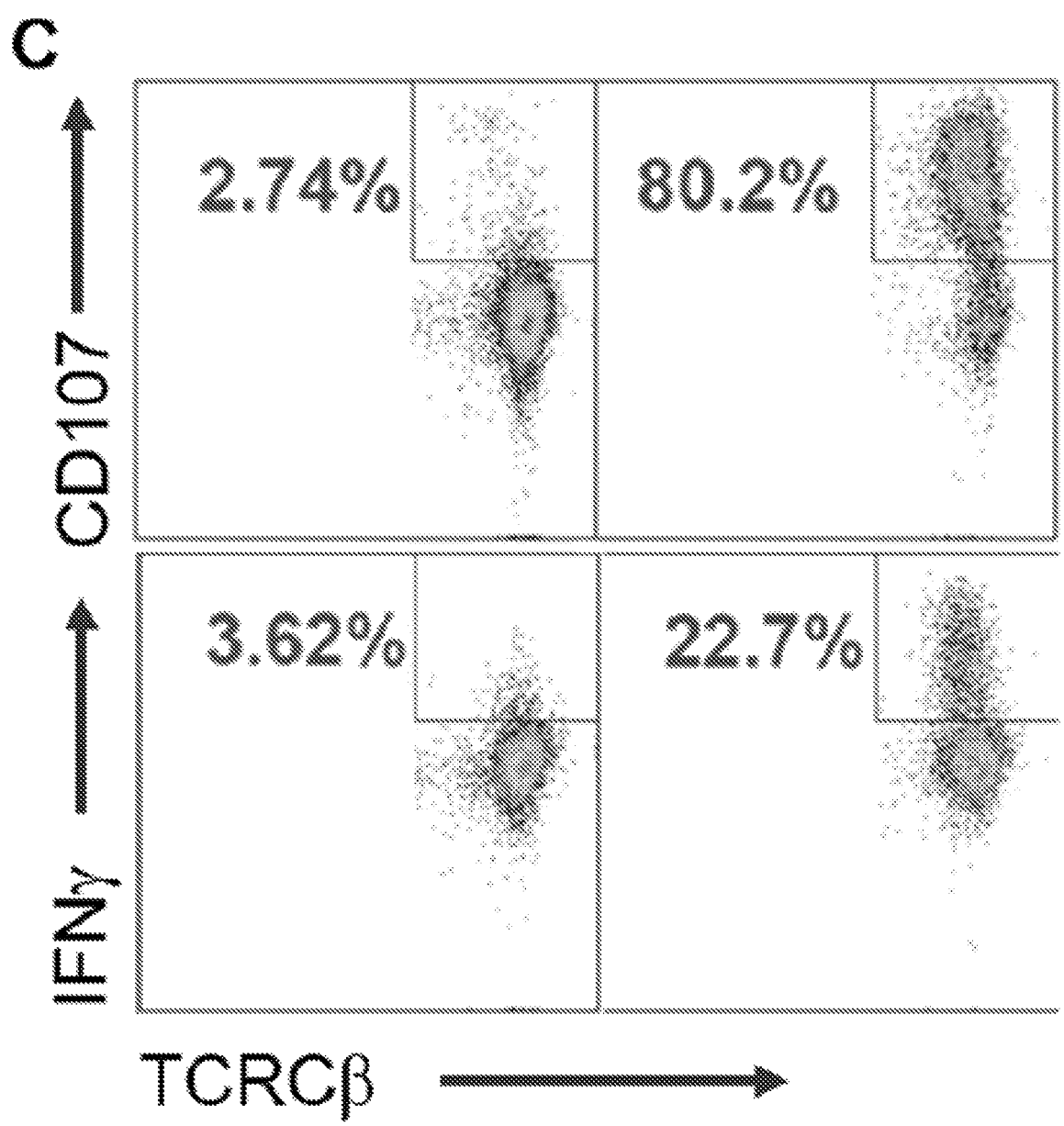

FIG.7 - continued
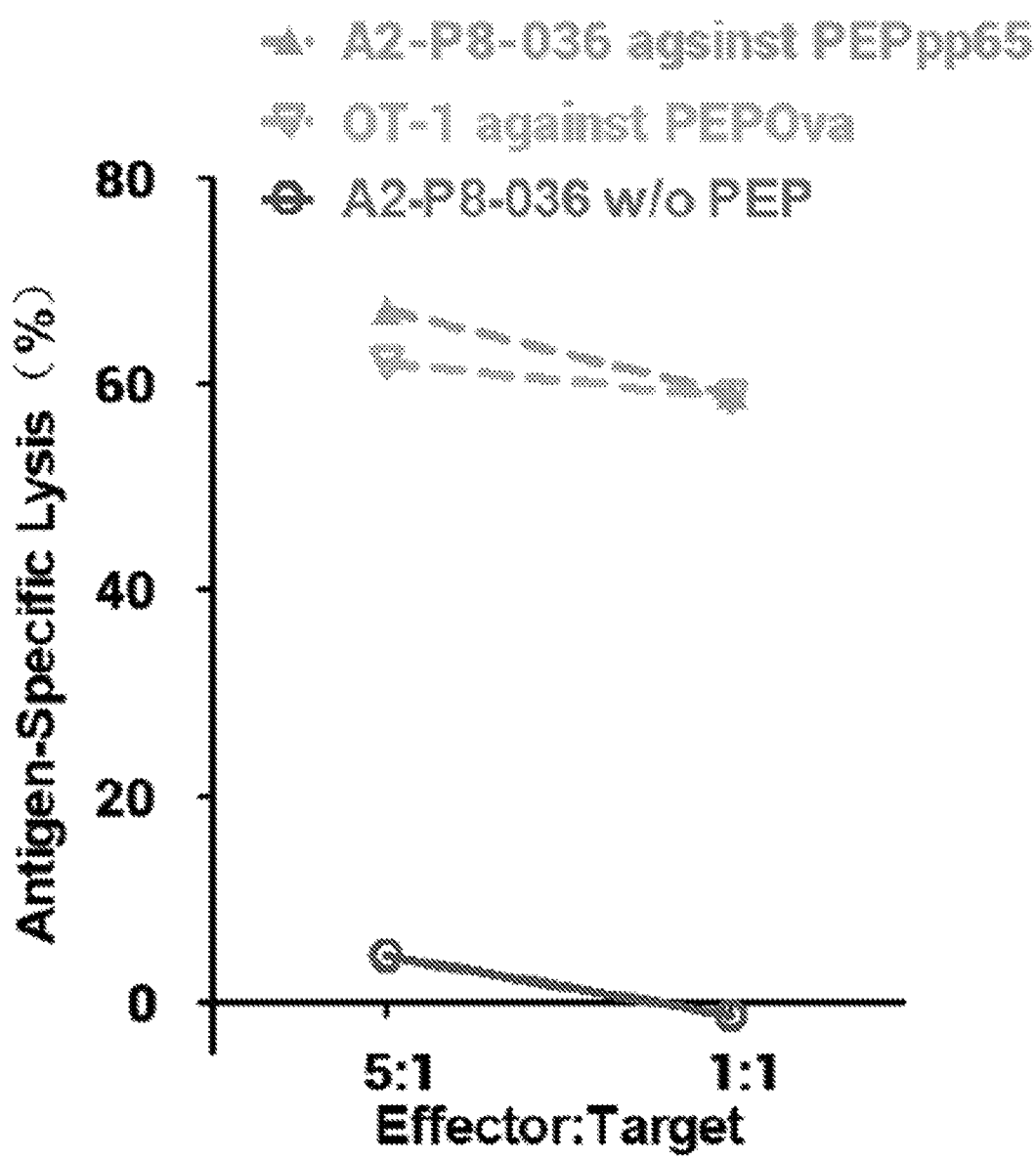

ANTI-LMP2 TCR-T CELL THERAPY FOR THE TREATMENT OF EBV-ASSOCIATED CANCERS

CROSS-REFERENCE TO RELATED APPLICATIONS

This application is U.S. national phase application under 35 U.S.C. § 371 of International Application No. PCT/US2019/063310, filed on Nov. 26, 2019, which claims the benefit of priority to U.S. Provisional Patent Application No. 62/771,653, filed on Nov. 27, 2018, the contents of each of which are incorporated herein by reference in their entirety.

BACKGROUND OF THE INVENTION

INCORPORATION BY REFERENCE OF SEQUENCE LISTING PROVIDED ELECTRONICALLY

This application contains a Sequence Listing submitted on 26 Nov. 2019 as an electronic.txt file named "19-2104-WO_SequenceListing_ST25". This Sequence Listing was created on 26 Nov. 2019 and has a size of 21680 bytes. The information contained in this electronic.txt file is incorporated in its entirety herein by reference.

Field of the Invention

The present disclosure provides methods of treating cancer. More particularly, the present disclosure provides compositions comprising T-cells comprising an engineered T-cell receptor (TCR) specific for Latent membrane protein 2 (LMP2), and methods of making and using the same, as well as, compositions comprising a TCR targeting a LMP2 antigen.

Description of the Related Art

T-cell receptor engineered T-cell therapy is a type of adoptive T-cell immunotherapy that genetically modifies T-cells to treat cancers. T-cell receptor engineered T-cell therapy has shown promise in treating solid tumors. One solid tumor type, nasopharyngeal carcinoma (NPC), is highly prevalent in South China and Southeast Asia with few treatment options for late stage disease. While the current standard therapies are limited by non-specific toxicity, NPC is often associated with Epstein-Barr virus (EBV) infection, making it an excellent target for adoptive immunotherapy.

Epstein-Barr virus (EBV) latent membrane protein 2 (LMP2) is a viral protein of the Epstein-Barr virus. The LMP2 antigen is a potential TCR T-cell target and thus targeted elimination of cells comprising an LMP2 antigen might have robust anti-tumor properties with limited toxicity against normal cells.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

TCR T-cell therapy is a type of treatment in which T-cells are isolated and are modified so the modified T-cells will attack cancer cells. Isolated T-cells are engineered to express a TCR specifically recognizes LMP2 on the patient's cancer cells. Large numbers of the TCR T-cells are grown in the laboratory and given to the patient, typically by infusion. The inventors have implementing next-generation immune cell therapy with antigen specificity-redirected T cells to shorten the time needed to generate T-cell populations that can be used in immunotherapy.

In an aspect, the present disclosure provides a population of T-cells comprising an engineered T-cell receptor (TCR), wherein the engineered TCR activates T-cells in response to a Latent membrane protein 2 (LMP2) antigen. In certain embodiments, the engineered TCR comprises the amino acid sequence of SEQ ID NO:03. In some embodiments, the engineered TCR comprises the amino acid sequence of SEQ ID NO:09. In certain embodiments, the LMP2 antigen comprises the sequence of SSCSSCPLSK (SEQ ID NO:01).

In certain embodiments, the population of T-cells comprises a therapeutically effective amount of cells for the treatment of a cancer comprising LMP2 in a subject. In some embodiments, the subject expresses human leukocyte antigen subtype A11 (HLA-A11).

In certain embodiments, at least a portion of the population of T-cells produces or has the potential to produce one or more cytokines. In some embodiments, the one or more cytokines are selected from the group consisting of IL-2, IFN-gamma, TNF-alpha, Granzyme A, Granzyme B, and GM-CSF.

In certain embodiments, the cancer is selected from the group consisting of nasopharyngeal carcinoma (NPC), lymphoma, gastric cancer, lung cancer, melanoma, breast cancer, prostate cancer, colon cancer, renal cell carcinoma, ovarian cancer, neuroblastoma, rhabdomyosarcoma, and leukemia. In some embodiments, the cancer is an EBV-associated cancer. In certain embodiments, the cancer is nasopharyngeal carcinoma (NPC). In certain embodiments, the cancer is lymphoma. In certain embodiments, the cancer is gastric cancer.

In another aspect, the present disclosure provides, a pharmaceutical composition comprising the population of T-cells as disclosed herein, and a pharmaceutically acceptable carrier. In certain embodiments, the pharmaceutically acceptable carrier supports maintenance of a therapeutically effective amount of cells for the treatment of a cancer comprising LMP2. In some embodiments, the pharmaceutical composition further comprising at least one therapeutic agent.

In yet another aspect, the present disclosure provides a method of treating a subject suffering from a cancer comprising LMP2, wherein the method comprises administering to the subject a therapeutically effective amount of the population of T-cells as disclosed herein, or the pharmaceutical composition as disclosed herein, wherein the administration induces an anti-tumor response to the cancer. In certain embodiments, the cancer is selected from group consisting of nasopharyngeal carcinoma (NPC), lymphoma, gastric cancer, lung cancer, melanoma, breast cancer, prostate cancer, colon cancer, renal cell carcinoma, ovarian cancer, neuroblastoma, rhabdomyosarcoma, and leukemia. In certain embodiments, the cancer is an EBV-associated cancer. In certain embodiments, the cancer is nasopharyngeal carcinoma (NPC). In certain embodiments, the cancer is lymphoma. In certain embodiments, the cancer is gastric cancer. In certain embodiments, the anti-tumor response results in a reduction of tumor volume by at least 5%, at least 10%, at least 20%, at least 30%, at least 40%, at least 50%, at least 60%, at least 70%, at least 80%, at least 90%, or 100%.

In another aspect, the present disclosure provides an isolated nucleic acid comprising a polynucleotide encoding an engineered TCR comprising the amino acid sequence of SEQ ID NO:03. In certain embodiments, the polynucleotide comprises the nucleic acid sequence of SEQ ID NO:08.

In another aspect, the present disclosure provides an isolated nucleic acid comprising a polynucleotide encoding an engineered TCR comprising the amino acid sequence of SEQ ID NO:09. In certain embodiments, the polynucleotide comprises the nucleic acid sequence of SEQ ID NO:14.

In yet another aspect, the present disclosure provides for vectors comprising the nucleic acids as disclosed herein. In certain embodiments, the vectors are selected from the group consisting of plasmids, cosmids, artificial chromosomes (such as a yeast artificial chromosome (YAC) or a bacterial artificial chromosome (BAC)), and viruses (such as a retrovirus, a lentivirus, an adenovirus, an adeno-associated virus (AAV), and a herpesvirus).

In an aspect, the present disclosure provides a method of preparing a population of T-cells, wherein the method comprises: (1) transfecting or transducing isolated T-cells with the isolated nucleic acids or vectors as disclosed herein; and (2) expanding the T-cells following transfection or transduction, wherein the T-cells are expanded by culturing in the presence of anti-CD3, anti-CD3/anti-CD28, or LMP protein presented by artificial APCs. In certain embodiments, the isolated T-cells are isolated from a human. In certain embodiments, the human is a subject suffering from a cancer comprising LMP2. In certain embodiments, the subject suffering from the cancer comprising LMP2 expresses human leukocyte antigen subtype A11 (HLA-A11).

In another aspect, the present disclosure provides a method of inhibiting the growth of a tumor comprising a Latent membrane protein 2 (LMP2) antigen in a patient in need thereof, wherein the method comprises administering to the patient a therapeutically effective amount of a population of T-cells comprising an engineered T cell receptor (TCR) with a TCR alpha chain having the sequence of SEQ ID NO: 4 or 10, and a TCR beta chain having the sequence of SEQ ID NO: 6 or 12, and wherein the growth of the tumor comprising the LMP2 antigen is inhibited. In certain embodiments, the tumor comprises a human leukocyte antigen subtype A11 (HLA-A11). In certain embodiments, the tumor is from an EBV-associated cancer. In certain embodiments, the cancer is nasopharyngeal carcinoma, lymphoma, or gastric cancer.

In certain embodiments, the engineered TCR comprises the TCR alpha chain of SEQ ID NO: 4, and the TCR beta chain of SEQ ID NO:6. In certain embodiments, the TCR alpha chain comprises a CDR3 alpha comprising the sequence AVVNNNDMRFG (SEQ ID NO:5), and the TCR beta chain comprises a CDR3 beta comprising the sequence of ASSPGRWYEQF (SEQ ID NO:7).

In certain embodiments, the engineered TCR comprises the TCR alpha chain of SEQ ID NO: 10, and the TCR beta chain of SEQ ID NO:12. In certain embodiments, the TCR alpha chain comprises a CDR3 alpha comprising the sequence AVLNNNDMRFG (SEQ ID NO:11), and the TCR beta chain comprises a CDR3 beta comprising the sequence of ASSQGRWYEAF (SEQ ID NO:13).

In yet another aspect, the present disclosure provides a engineered T-cell receptor (TCR), wherein the TCR comprises an amino acid that shares at least 90% sequence identity to the sequence as set forth in SEQ ID NO:03. In certain embodiments, the TCR comprises a TCR alpha chain of SEQ ID NO: 4 and a TCR beta chain of SEQ ID NO:6. In certain embodiments, the TCR alpha chain comprises a CDR3 alpha comprising the sequence AVVNNNDMRFG (SEQ ID NO:5), and the TCR beta chain comprises a CDR3 beta comprising the sequence of ASSPGRWYEQF (SEQ ID NO:7).

In yet another aspect, the present disclosure provides an engineered T-cell receptor (TCR), wherein the TCR comprises an amino acid that shares at least 90% sequence identity to the sequence as set forth in SEQ ID NO:09. In certain embodiments, the TCR comprises a TCR alpha chain of SEQ ID NO: 10 and a TCR beta chain of SEQ ID NO:12. In certain embodiments, the TCR alpha chain comprises a CDR3 alpha comprising the sequence AVLNNNDMRFG (SEQ ID NO:11), and the TCR beta chain comprises a CDR3 beta comprising the sequence of ASSQGRWYEAF (SEQ ID NO:13).

In certain embodiments, the engineered TCRs as disclosed herein specifically bind to a LMP2 antigen. In certain embodiments, the LMP2 antigen comprises SSCSSCPLSK (SEQ ID NO:1).

In an aspect, the present disclosure provides a pharmaceutical composition comprising a population of T-cells expressing the engineered TCRs as disclosed herein, and a pharmaceutically acceptable carrier.

In another aspect, the present disclosure provides a method of inducing a T-cell response in a subject suffering from a cancer comprising LMP2, wherein the method comprises administering to the subject a therapeutically effective amount of a population of T-cells comprising the engineered TCRs as disclosed herein, or the pharmaceutical compositions as disclosed here, wherein the administration induces an anti-tumor response to the cancer. In certain embodiments, the cancer is selected from group consisting of nasopharyngeal carcinoma (NPC), lymphoma, gastric cancer, lung cancer, melanoma, breast cancer, prostate cancer, colon cancer, renal cell carcinoma, ovarian cancer, neuroblastoma, rhabdomyosarcoma, and leukemia. In certain embodiments, the cancer is an EBV-associated cancer. In certain embodiments, the cancer is nasopharyngeal carcinoma (NPC). In certain embodiments, the cancer is lymphoma. In certain embodiments, the cancer is gastric cancer.

Another aspect of the present disclosure provides all that is described and illustrated herein.

BRIEF DESCRIPTION OF THE DRAWINGS

The foregoing aspects and other features of the disclosure are explained in the following description, taken in connection with the accompanying drawings, herein:

FIG. 1A-1B are flow cytometric results showing the expression and activity of candidate LMP2-A11 TCRs. (A) Candidate TCR sequences were cloned into retroviral vectors that were transduced into Jurkat cells, the percentages of TCRb-positive cells are indicated. (B) Jurkat cell lines in FIG. 1A were co-cultured with Ramos lymphoma cells engineered to express the HLA-A11-LMP2 peptide linker. T cell activation was quantified by measuring CD69 expression. The TCR identified as TCR-NPC-A11-03 was identified as LMP2-specific.

FIG. 7A-7D are graphs and flow cytometric analysis showing PEPCMV-HLA-A2-specific TCR cloning and TCR-T validation. Single T cell RNASeq was performed to clone TCRs recognizing the CMVpp65 epitope presented by HLA-A2 donor. (A) V segment usages of cloned TCR α and β chains. (B) Human TCR-T cells generated by retroviral transduction. (C) Antigen-specific activation of CMVpp65-TCR-T cells. Left, unstimulated; right, antigen simulated. CD107 is used as a marker for antigen-induced degranulation, a critical step in T cell-mediated cytolysis. (D) Antigen specific killing by A2-P8-036 TCR-T. Mouse OT-1 transgenic T cells were used as a positive control; target cells without loading CMVpp65 peptide antigen were used as a negative control.

DETAILED DESCRIPTION

Figures 2A, 2B:
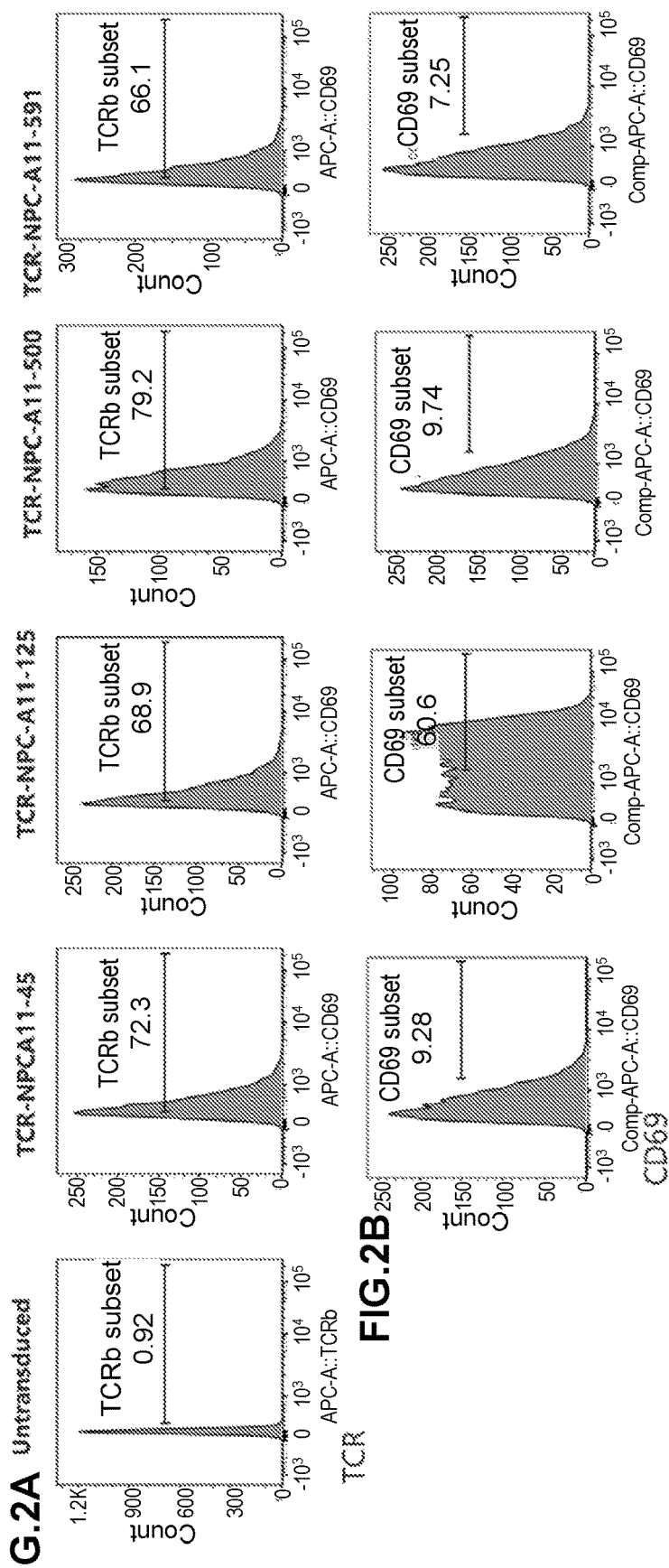
FIG. 2A-2B are flow cytometric results showing the expression and activity of candidate LMP2-A11 TCRs. (A) Candidate TCR sequences were cloned into retroviral vectors that were transduced into Jurkat cells, the percentages of TCRb-positive cells are indicated. (B) Jurkat cell lines in 1 A were co-cultured with Ramos lymphoma cells engineered to express the HLA-A11-LMP2 peptide linker. T cell activation was quantified by measuring CD69 expression. The TCR identified as TCR-NPC-A11-125 was identified as LMP2-specific.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

The term "about" is used to provide flexibility to a numerical range endpoint by providing that a given value may be "slightly above" or "slightly below" the endpoint without affecting the desired result.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps. Embodiments recited as "including." "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

Definitions

As used herein, "treat", "treatment", "therapy", and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The terms "effective amount" or "therapeutically effective amount" refer to an amount sufficient to effect beneficial or desirable biological and/or clinical results. An "effective amount" or "therapeutically effective amount" can be determined by a skilled team of health professionals, and can include use of imaging tests, biomarker tests, or additional tests. Regarding cancer, administration of a therapeutically effective amount prevents metastasis of the cancer, result in a decrease in the size or mass of a solid tumor, or inhibits proliferation or growth of the cancer, or result in necrosis of a tumor.

The term "disease" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

As is known in the art, cancer is generally considered as uncontrolled cell growth. The compositions and methods of the present invention can be used to treat any cancer, and any metastases thereof, that expresses LMP2. Examples include, but are not limited to, nasopharyngeal carcinoma (NPC), lymphoma, gastric cancer, lung cancer, melanoma, breast cancer, prostate cancer, colon cancer, renal cell carcinoma, ovarian cancer, neuroblastoma, rhabdomyosarcoma, and leukemia. In certain embodiments, the cancer is nasopharyngeal carcinoma. In some embodiments, the cancer is lymphoma. In some embodiments, the cancer is gastric cancer. In certain embodiments, the cancer is an EBV-associated cancer or an EBV-positive cancer, for example, EBV-positive Hodgkin's Lymphoma, EBV-positive Burkitt Lymphoma, EBV-positive nasopharyngeal carcinoma, or EBV-positive gastric cancer.

Nasopharyngeal carcinoma (NPC) is a multifactorial malignancy associated with both genetic and environmental factors (for example, the Epstein-Barr virus has been implicated). The viral influence is associated with infection with Epstein-Barr virus (EBV; also referred to as human herpesvirus 4), and EBV is one of the most common viruses (for example, about 95% of all people in the U.S. are exposed to this virus by the time they are 30-40 years old). Thus, the high frequency of NPC in southeast Asian individuals, especially persons of Cantonese Chinese ancestry, suggests a strong genetic factor predisposing to the development of the disorder. In areas with high incidence, NPC clusters in families, which suggests that both geography and genetics may influence disease risk. NPC can be treated by surgery, by chemotherapy, or by radiotherapy. There are different forms of radiation therapy, including 3D conformal radiation therapy, intensity-modulated radiation therapy, particle beam therapy and brachytherapy, which are commonly used in the treatments of cancers of the head and neck. The expression of EBV latent proteins within undifferentiated nasopharyngeal carcinoma can be potentially exploited for immune-based therapies as disclosed herein.

As used herein, the terms "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In certain embodiments, the subject is a human patient that is suspected of having cancer, has cancer, or suffers from cancer. In an embodiment, the human is a subject suspected of having a cancer comprising LMP2. In another embodiment, the human is a subject having a cancer comprising LMP2. In yet another embodiment, the human is a subject suffering from a cancer comprising LMP2. In certain embodiments, the subject is a human suffering from an LMP2-associated cancer. In certain embodiments, the subject is a human suffering from an EBV-associated cancer. In certain embodiments, the patient is EBV serum positive. In certain embodiments, the LMP2 antigen is in complex with an MHC class I molecule having human leukocyte antigen subtype A11 (HLA-A11).

As used herein, the terms "latent membrane protein 2" and "LMP2" refer to EBV antigen latent membrane protein 2 (LMP2). LMP2 is expressed in many EBV-associated cancers. In certain embodiments, the LMP2 antigen is in complex with an MHC class I molecule having human leukocyte antigen subtype A1 (HLA-A11). LMP2 can exist in two isoforms, LMP2A or LMP2B. LMP2A is an EBV-encoded protein with three domains: (a) an N-terminal cytoplasmic domain, which has PY motifs that bind to WW domain-containing E3 ubiquitin ligases and an ITAM that binds to SH2 domain-containing proteins, (b) a transmembrane domain with 12 transmembrane segments that localizes LMP2A in cellular membranes, and (c) a 27-amino acid C-terminal domain which mediates homodimerization and heterodimerization of LMP2 protein isoforms. LMP2B, unlike LMP2A, does not contain the N-terminal 1-119 amino acids of the cytoplasmic signaling domain. In some embodiments, the LMP2 antigen can be a fragment from the amino acid sequence of SEQ ID NO:02. In some embodiments, the LMP2 antigen can be SSCSSCPLSK (SEQ ID NO:01)

```
>sp|P13285|LMP2_EBVB9 Latent membrane protein 2
                                       (SEQ ID NO: 02)
MGSLEMVPMGAGPPSPGGDPDGYDGGNNSQYPSASGSSGNTPTPPNDEER

ESNEEPPPPYEDPYWGNGDRHSDYQPLGTQDQSLYLGLQHDGNDGLPPPP

YSPRDDSSQHIYEEAGRGSMNPVCLPVIVAPYLFWLAAIAASCFTASVST

VVTATGLALSLLLLAAVASSYAAAQRKLLTPVTVLTAVVTFFAICLTWRI

EDPPFNSLLFALLAAAGGLQGIYVLVMLVLLILAYRRRWRRLTVCGGIMF

LACVLVLIVDAVLQLSPLLGAVTVVSMTLLLLAFVLWLSSPGGLGTLGAA

LLTLAAALALLASLILGTLNLTTMFLLMLLWTLVVLLICSSCSSCPLSKI

LLARLFLYALALLLLASALIAGGSILQTNFKSLSSTEFIPNLFCMLLLIV

AGILFILAILTEWGSGNRTYGPVFMCLGGLLTMVAGAVWLTVMSNTLLSA

WILTAGFLIFLIGFALFGVIRCCRYCCYYCLTLESEERPPTPYRNTV
```

The terms "T-cell receptor" or "TCR" or "engineered TCR" refer to a molecule found on the surface of T-cells that is responsible for recognizing an antigen displayed on the surface of antigen-presenting cells (APCs). Each T-cell expresses a unique TCR that is generated by randomly assorting genes ensuring that T-cells can respond to almost any infection. TCRs can also recognize tumor-specific proteins (antigens) from the inside of cells. When tumor-specific proteins (i.e. LMP2) are broken into fragments, they show up on the cell surface with the major histocompatibility complex (MHC). MHC class I molecules present peptide antigens that are derived from intracellular proteins. TCRs can be engineered to recognize a tumor-specific protein fragment/MHC combination. In certain embodiments, the LMP2 antigen is in complex with an MHC class I molecule having human leukocyte antigen subtype A11 (HLA-A11). TCR structure is composed of two different protein chains comprising an alpha (α) chain and a beta (β) chain. In certain embodiments, the TCR can have one or more amino acid substitutions, deletions, insertions, or modifications compared to a naturally occurring sequence, so long as the TCR retains its ability to form TCRs in transfected T cells and maintain the ability to recognize the LMP2 antigen, and participate in immunologically-relevant cytokine signaling. The engineered TCRs preferably also bind target cells displaying the relevant tumor-associated peptide with high avidity, and optionally mediate efficient killing of target cells presenting the relevant antigen (LMP2). The heterodimeric TCR protein normally consisting of the highly variable alpha- and beta-chains expressed as part of a complex with the invariant CD3 chain molecules. The variable domains of both the TCR α-chain and β-chain each have three hyper-variable or complementarity determining regions (CDRs). In one embodiment, the TCR comprises TCR-NPC-A11-003. In another embodiment, the TCR comprises TCR-NPC-A11-125.

TCR A11-003 sequences:

TCR A11-003 Amino Acid
(SEQ ID NO: 03)
MKRILGALLGLLSAQVCCVRGIQVEQSPPDLILQEGANSTLRCNFSDSVN
NLQWFHQNPWGQLINLFYIPSGTKQNGRLSATTVATERYSLLYISSSQTT
DSGVYFCAVVNNNDMRFGAGTRLTVKPDIQNPEPAVYQLKDPRSQDSTLC
LFTDFDSQINVPKTMESGTFITDKTVLDMKAMDSKSNGAIAWSNQTSFTC
QDIFKETNACYPSSDVPCDATLTEKSFETDMNLNFQNLSVMGRLILLLKV
AGFNLLMTLRLWSSRAKRGSGATNFSLLKQAGDVEENPGPMGCRLLCCAV
LCLLGAVPIDTEVTQTPKHLVMGMTNKKSLKCEQHMGHRAMYWYKQKAKK
PPELMFVYSYEKLSINESVPSRFSPECPNSSLLNLHLHALQPEDSALYLC
ASSPGRWYEQFFGPGTRLTVL TCR A11-03 Variable alpha chain Amino Acid
(SEQ ID NO: 04)
MKRILGALLGLLSAQVCCVRGIQVEQSPPDLILQEGANSTLRCNFSDSVN
NLQWHQNPWGQLINLFYIPSGTKQNGRLSATTVATERYSLLYISSSQTTD
SGVYFCAVVNNNDMRFGAGTRLTVKP TCR A11-003 Variable CDR3 alpha Amino Acid
(SEQ ID NO: 05)
AVVNNNDMRFG TCR A11-003 Variable beta chain Amino Acid
(SEQ ID NO: 06)
MGCRLLCCAVLCLLGAVPIDTEVTQTPKHLVMGMTNKKSLKCEQHMGHRA
MYWYKQKAKKPPELMFVYSYEKLSINESVPSRFSPECPNSSLLNLHLHAL
QPEDSALYLCASSPGRWYEQFFGPGTRLTVL TCR A11-003 Variable CDR3 beta Amino Acid
(SEQ ID NO: 07)
ASSPGRWYEQF TCR A11-003 Nucleic Acid
(SEQ ID NO: 08)
ATGAAGAGAATCCTGGGCGCTCTGCTGGGACTGCTGTCTGCTCAAGTGTG
CTGTGTGCGGGGCATCCAGGTGGAACAAAGCCCTCCTGACCTGATCCTGC
AAGAGGGCGCCAATAGCACCCTGCGGTGCAACTTTAGCGACAGCGTGAAC
AACCTGCAGTGGTTCCACCAGAATCCTTGGGGCCAGCTGATCAACCTGTT
CTACATCCCCAGCGGCACCAAGCAGAACGGCAGACTGTCTGCTACCACCG
TGGCCACCGAGAGATACAGCCTGCTGTACATCAGCAGCAGCCAGACCACA
GACAGCGGCGTGTACTTTTGCGCCGTGGTCAACAACAACGACATGAGATT
CGGAGCCGGCACCAGACTGACCGTGAAGCCCGATATCCAGAATCCAGAGC
CTGCCGTGTACCAGCTGAAGGACCCTAGAAGCCAGGACAGCACCCTGTGC
CTGTTCACCGACTTCGACAGCCAGATCAACGTGCCCAAGACCATGGAAAG
CGGCACCTTCATCACCGACAAGACCGTGCTGGACATGAAGGCCATGGACA
GCAAGAGCAACGGCGCCATTGCCTGGTCCAACCAGACCAGCTTCACATGC
CAGGACATCTTCAAAGAGACAAACGCCTGCTATCCCAGCAGCGACGTGCC
CTGTGATGCCACACTGACCGAGAAGTCCTTCGAGACAGACATGAACCTGA
ACTTCCAGAACCTGAGCGTGATGGGCCTGCGCATCCTGCTGCTTAAAGTG
GCCGGCTTCAACCTGCTGATGACCCTGAGACTGTGGTCCAGCAGGGCCAA
GAGAGGAAGCGGCGCCACAAACTTTAGCCTGCTGAAACAGGCCGGCGACG
TGGAAGAAAACCCTGGACCTATGGGCTGCAGACTGCTGTGTTGTGCCGTG
CTGTGTCTGCTGGGCGCCGTGCCTATTGACACCGAAGTGACCCAGACACC
TAAGCACCTGGTCATGGGCATGACAAACAAGAAAAGCCTGAAGTGCGAGC
AGCACATGGGCCACAGAGCCATGTACTGGTACAAGCAGAAGGCCAAGAAA
CCTCCAGAGCTGATGTTCGTGTACAGCTACGAGAAGCTGAGCATCAACGA
GAGCGTGCCCAGCAGGTTCAGCCCTGAGTGTCCTAATAGCTCCCTGCTGA
ATCTGCATCTGCACGCCCTGCAGCCTGAGGATTCTGCCCTGTACCTGTGT
GCCAGCTCTCCCGGACGTTGGTACGAGCAGTTTTTCGGCCCTGGCACACG
GCTGACAGTTCTG TCR A11-125 sequences:

TCR A11-125 Amino Acid
(SEQ ID NO: 09)
MKRILGALLGLLSAQVCCVRGIQVEQSPPDLILQEGANSTLRCNFSDSVN
NLQWFHQNPWGQLINLFYIPSGTKQNGRLSATTVATERYSLLYISSSQTT
DSGVYFCAVLNNNDMRFGAGTRLTVKPDIQNPEPAVYQLKDPRSQDSTLC
LFTDFDSQINVPKTMESGTFITDKTVLDMKAMDSKSNGAIAWSNQTSFTC
QDIFKETNACYPSSDVPCDATLTEKSFETDMNLNFQNLSVMGLRILLLKV
AGFNLLMTLRLWSSRAKRGSGATNFSLLKQAGDVEENPGPMGCRLLCCAV
LCLLGAVPIDTEVTQTPKHLVMGMTNKKSLKCEQHMGHRAMYWYKQKAKK
PPELMFVYSYEKLSINESVPSRFSPECPNSSLLNLHLHALQPEDSALYLC
ASSQGRWYEAFFGQGTRLTVV TCR A11-125 Variable alpha Amino Acid
(SEQ ID NO: 10)
MKRILGALLGLLSAQVCCVRGIQVEQSPPDLILQEGANSTLRCNFSDSVN
NLQWFHQNPWGQLINLFYIPSGTKQNGRLSATTVATERYSLLYISSSQTT
DSGVYFCAVLNNNDMRFGAGTRLTVKP TCR A11-125 Variable CDR3 alpha Amino Acid
(SEQ ID NO: 11)
AVLNNNDMRFG TCR A11-125 Variable beta chain Amino Acid
(SEQ ID NO: 12)
MGCRLLCCAVLCLLGAVPIDTEVTQTPKHLVMGMTNKKSLKCEQHMGHRA
MYWYKQKAKKPPELMFVYSYEKLSINESVPSRFSPECPNSSLLNLHLHAL
QPEDSALYLCASSQGRWYEAFFGQGTRLTVV TCR A11-125 Variable CDR3 beta Amino Acid
(SEQ ID NO: 13)
ASSQGRWYEAF TCR A11-125 Nucleic Acid
(SEQ ID NO: 14)
ATGAAGAGAATCCTGGGCGCTCTGCTGGGACTGCTGTCTGCTCAAGTGTG
CTGTGTGCGGGGCATCCAGGTGGAACAGTCTCCACCAGACCTGATCCTGC
AAGAGGGCGCCAATAGCACCCTGCGGTGCAACTTTAGCGACAGCGTGAAC
AACCTGCAGTGGTTCCACCAGAATCCTTGGGGCCAGCTGATCAACCTGTT
CTACATCCCCAGCGGCACCAAGCAGAACGGCAGACTGTCTGCTACCACCG
TGGCCACCGAGAGATACAGCCTGCTGTACATCAGCAGCAGCCAGACCACA
GACAGCGGCGTGTACTTTGCGCCGTGCTGAACAACAACGACATGAGATT -continued
```
CGGAGCCGGCACCAGACTGACCGTGAAGCCCGATATCCAGAATCCAGAGC

CTGCCGTGTACCAGCTGAAGGACCCTAGAAGCCAGGACAGCACCCTGTGC

CTGTTCACCGACTTCGACAGCCAGATCAACGTGCCCAAGACCATGGAAAG

CGGCACCTTCATCACCGACAAGACCGTGCTGGACATGAAGGCCATGGACA

GCAAGAGCAACGGCGCCATTGCCTGGTCCAACCAGACCAGCTTCACATGC

CAGGACATCTTCAAAGAGACAAACGCCTGCTATCCCAGCAGCGACGTGCC

CTGTGATGCCACACTGACCGAGAAGTCCTTCGAGACAGACATGAACCTGA

ACTTCCAGAACCTGAGCGTGATGGGCCTGCGCATCCTGCTGCTTAAAGTG

GCCGGCTTCAACCTGCTGATGACCCTGAGACTGTGGTCCAGCAGGGCCAA

GAGAGGAAGCGGCGCCACAAACTTTAGCCTGCTGAAACAGGCCGGCGACG

TGGAAGAAAACCCTGGACCTATGGGCTGCAGACTGCTGTGTTGTGCCGTG

CTGTGTCTGCTGGGCGCCGTGCCTATTGACACCGAAGTGACCCAGACACC

TAAGCACCTGGTCATGGGCATGACAAACAAGAAAAGCCTGAAGTGCGAGC

AGCACATGGGCCACAGAGCCATGTACTGGTACAAGCAGAAGGCCAAGAAA

CCTCCTGAGCTGATGTTCGTGTACAGCTACGAGAAGCTGAGCATCAACGA

GAGCGTGCCCAGCAGGTTCAGCCCTGAGTGTCCTAATAGCTCCCTGCTGA

ATCTGCATCTGCACGCCCTGCAGCCTGAGGATTCTGCCCTGTATCTGTGC

GCCAGCTCTCAAGGACGTTGGTACGAGGCCTTCTTCGGCCAAGGCACAAG

GCTGACAGTGGTG
```

The term "TCR-T cells" as used herein refer to a T-cell or population of T-cells, which have been selected, isolated and/or characterized through molecular biological methods to express an engineered T-cell receptor as disclosed herein that is capable of being activated in response to an antigen of interest. In some embodiments, the T-cell population comprises peripheral blood mononuclear cells (PBMC's), which are any peripheral blood cell having a round nucleus. PBMC's can comprise of lymphocytes (T cells, B cells, NK cells), monocytes, and granulocytes (neutrophils, basophils, and eosinophils). In humans, lymphocytes make up the majority of the PBMC population, followed by monocytes, and only a small percentage of dendritic cells. In some embodiments, the T-cell population is isolated from PBMCs. In some embodiments, the TCR may be modified on any cell comprising a TCR, including, for example, a helper T cell, a cytotoxic T cell, a memory T cell, regulatory T cell, natural killer T cell, and gamma delta T cell. In certain embodiments, the T-cell receptor comprises a sequence capable of activating in response to a LMP2 antigen. In an embodiment, the TCR comprises TCR-NPC-A11-003. In another embodiment, the TCR comprises TCR-NPC-A11-125. Techniques for engineering and expressing T cell receptors include, but are not limited to, the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, one skilled in the art will understand that an antigen need not be encoded solely by a full length nucleotide sequence of a gene. It is readily apparent that an antigen can be generated synthesized or can be derived from a biological sample. Such a biological sample can include, but is not limited to a tissue sample, a tumor sample, a cell or a biological fluid. In certain embodiments, the antigen of interest comprises a fragment of the LMP2 protein (SEQ ID NO:2). In some embodiments, the antigen of interest comprises SSCSSCPLSK (SEQ ID NO:1).

As used herein, the terms "specifically binds" or "selectively binds", when referring to an antibody/antigen, TCR/epitope, ligand/receptor, nucleic acid/complementary nucleic acid, or other binding pair (e.g., a cytokine to a cytokine receptor) indicate a binding reaction which is determinative of the presence of the protein in a heterogeneous population of proteins and other biologics. Thus, under designated conditions, a specified TCR or binding domain thereof binds to a particular antigen and does not bind in a significant amount to other proteins present in the sample. In particular, the engineered TCR as disclosed herein selectively recognizes or binds to preferably only one specific epitope (LMP2 antigen) and preferably shows no or substantially no cross-reactivity to another epitope, wherein said epitope is unique for one protein (LMP2), such that the antigen recognizing construct shows no or substantially no cross-reactivity to another epitope and another protein. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound. In certain embodiments, the engineered T cell receptor, or derivative or fragment thereof, specifically binds a LMP2 antigen. A derivative or fragment of the TCR retains the antigen binding/recognizing ability of the parent molecule, in particular its specificity and/or selectivity. Such binding functionality may be retained by the presence of a CDR3 region.

The term "administration" as it applies to a human, primate, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can also refer to, for example, therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" can also encompass in vitro and ex vivo treatments, e.g., of a cell, by a reagent, diagnostic, binding composition, or by another cell. Routes of administration can include, but are not limited to, intravenous administration or infusion techniques. Infusion techniques can involve the administration of the population of activated T-cells through a needle or catheter. Typically, infusion means that the population of activated T-cells is administered intravenously or subcutaneously. In certain embodiments, the population of activated T-cells is administered systemically. In certain embodiments, the population of activated T-cells is administered intravenously (i.e., by intravenous (IV) injection). Preferred routes of administration are intraperitoneally or intravenously.

TCR-T Cells

The present disclosure relates, in part, to the preparation and use in recipients of TCR-T cell-derived effector cells which are capable of being activated in response to an antigen of interest (for example, LMP2). One aspect of the present disclosure provides a TCR-T cell-derived effector cell population comprising, consisting of, or consisting essentially of a population of T cells expressing a T cell receptor (TCR), the TCR comprising a sequence capable of activating in response to a LMP2 antigen. In one embodiment, the TCR comprises TCR-NPC-A11-003. In another embodiment, the TCR comprises TCR-NPC-A11-125.

T-cells used in the methods disclosed herein can be isolated by methods known in the art, including commercially available isolation methods. Sources for the T-cells include, but are not limited to, peripheral blood, umbilical cord blood, bone marrow, or other sources of hematopoietic cells. Various techniques can be employed to separate the cells to isolate or enrich for desired T-cells. Furthermore, methods for expanding T-cells are well known in the art (see, for example see, for example, Cartellieri et al., A Novel Ex Vivo Isolation and Expansion Procedure for Chimeric Antigen Receptor Engrafted Human T Cells, 2014). Methods for isolating and expanding regulatory T-cells are also commercially available (see, for example, BD Biosciences, San Jose, Calif.; STEMCELL Technologies Inc., Vancouver, Canada: eBioscience, San Diego, Calif.; Invitrogen, Carlsbad, Calif.). The term "expand" as used herein refers to increasing in number, as in an increase in the number of T-cells. In an embodiment, the T-cells can be expanded ex vivo to increase in number relative to the number originally present in the culture. In another embodiment, the T-cells are expanded ex vivo to increase in number relative to other cell types in the culture. The term "ex vivo," as used herein, refers to cells that have been removed from a living organism (e.g., a human) and propagated outside the organism (e.g., in a culture dish, test tube, or bioreactor). In some embodiments, the T-cells can be expanded by culturing in the presence of IL-2. In certain embodiments, the T-cells can be expanded by culturing in the presence of anti-CD3 antibodies and/or anti-CD28 antibodies. In some embodiments, the T-cells can be expanded by culturing in the presence of IL-2, and by culturing in the presence of anti-CD3 antibodies and/or anti-CD28 antibodies.

Procedures for separation of cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient techniques.

The isolated T-cells can be autologous or non-autologous to the subject to which they are administered in the methods of treatment of as disclosed herein. Autologous cells are isolated from the subject to which the population of T-cells comprising the engineered TCR are to be administered. In certain embodiments, autologous cells are isolated from the subject to which the isolated and expanded cells comprising the engineered TCR are to be administered. In some embodiments, the cells can be obtained by leukapheresis, where leukocytes are selectively removed from withdrawn blood, made recombinant, and then re-transfused into the donor subject. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. In an embodiment, the population of T-cells is matched for human leukocyte antigen A11 (HLA-A11). For both autologous and non-autologous cells, the cells can optionally be cryopreserved until ready to be used for genetic manipulation and/or administration to a subject using methods well known in the art.

Because cytokine release is a necessary consequence of T-cell activation and efficacy, for effective TCR T-cell-based therapy, it is preferred that at least a portion of the activated T-cells produce one or more cytokines or are capable of producing one or more cytokines, such as one or more cytokines selected from the group consisting of IL-2, TNF-α (alpha), and IFN-γ (gamma), Granzyme A, Granzyme B, GM-CSF, IL-1, IL-10, and IL-1β. Additionally, at least a portion of the population of the population of T-cells expresses one or more surface markers selected from the group consisting of CD2, CD3, CD4, CD8, CD28, CTLA4, CD16/CD56, CD18, CD25, CD40 ligand (gp39), CD69, MHC Class I, MHC Class II, CD54, LFA-1, and VLA-4.

Therapeutic Compositions

The cell compositions T-cell populations as described herein can be administered to a subject, either alone or in combination with a pharmaceutically acceptable carrier, in an amount sufficient to induce an appropriate anti-tumor response. The response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

The present disclosure provides methods of generating an anti-tumor immunity in a subject by administering to the subject an effective amount of a TCR T-cell population. An "effective amount" as used herein means an amount which provides a therapeutic or prophylactic benefit. Effective amounts of TCR T-cells can be determined by a physician with consideration of individual differences in age, weight, tumor size, extent of infection or metastasis, and condition of the patient (subject). It can generally be stated that a pharmaceutical composition comprising the population of T-cells comprising the anti-LMP2 engineered TCRs as described herein may be administered at a dosage of $10^4$ to $10^{11}$ cells/kg body weight, preferably $10^5$ to $10^{10}$ cells/kg body weight, including all integer values within those ranges. In some embodiments, the population of T-cells is administered by infusion of about 2-$10^8$ TCR-T cells. In some embodiments, about $5 \times 10^6$ to about $5 \times 10^7$ TCR-T cells per kg of patient is administered. T-cell compositions and T-cell populations may also be administered multiple times at these dosages. The cells can be administered by using infusion techniques that are commonly known in immunotherapy (see, e.g., Rosenberg et al, *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

An effective amount of the cell compositions comprising a population of T-cells expressing the T-cell receptor as described herein, may be given in one administration of a dose of the population of T-cells, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, doses of the population of T-cells expressing the engineered TCRs as disclosed herein. In certain embodiments, three doses are administered. Where there is more than one administration of a dose, the administration of the doses can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administration of the doses can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, or more, and any combination thereof. The invention is not limited to dosing intervals that are spaced equally in time, but also can encompass doses at non-equal intervals, such as a priming schedule consisting of administration at, for example, 1 day, 4 days, 7 days, and 25 days.

As used herein, the terms "pharmaceutically acceptable carrier" or "pharmaceutically acceptable excipient" refer to any material which, when combined with the population of T-cells comprising the engineered TCRs, allow the population of T-cells to retain biological activity. Examples include, but are not limited to, any of the standard pharmaceutical carriers such as a phosphate buffered saline solution, water, emulsions such as oil/water emulsion, amino acid-based buffers, or bicarbonate buffered solutions, and various types of wetting agents. In certain embodiments, the carrier does not produce adverse, allergic, or other untoward reactions when administered to a subject. In some embodiments, the pharmaceutical composition comprising the carrier is free of pyrogens, as well as other impurities that could be harmful to the subject. Pharmaceutically acceptable carriers can include any and all solvents, dispersion media, coatings, antibacterial and antifungal agents, isotonic and absorption delaying agents and the like; the use of which are well known in the art. Acceptable carriers, excipients or stabilizers are nontoxic to recipients and are preferably inert at the dosages and concentrations employed, and include buffers such as phosphate, citrate, or other organic acids; antioxidants such as ascorbic acid, low molecular weight polypeptides; proteins, such as scrum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG). Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005). The carrier selected and the amount of carrier used can depend upon the mode of administration.

An "effective amount" for a particular subject/patient can vary depending on factors such as the condition or cancer being treated, the overall health of the patient, the route and dose of administration and the severity of side effects. Guidance for methods of treatment and diagnosis is available (see, e.g., Maynard, et al. (1996) A Handbook of SOPs for Good Clinical Practice. Interpharm Press, Boca Raton, Fla.; Dent (2001) Good Laboratory and Good Clinical Practice, Urch Publ., London, UK). Determination of the number of cells to be administered will be made by one of skill in the art, and will in part be dependent on the extent and severity of cancer, and whether the transfected cells are being administered for treatment of existing cancer or prevention of cancer. The preparation of the pharmaceutical composition containing the population of T-cells comprising the engineered TCRs will be known to those of skill in the art in light of the present disclosure.

The population of T-cells expressing an engineered TCR of the present disclosure can be administered in a dose, or dosages, where each dose comprises at least 100 cells/kg body weight; at least 1,000 cells/kg body weight; at least 10,000 cells/kg body weight; at least 100,000 cells/kg body weight; at least 1,000,000 cells/kg body weight; at least 10,000,000 cells/kg body weight; at least 100,000,000 cells/kg body weight; at least $1\times10^9$ cells/kg body weight; at least $10\times10^9$ cells/kg body weight; at least $100\times10^9$ cells/kg body weight; or at least $1\times10^{12}$ cells/kg body weight.

A dosing schedule of, for example, once/week, twice/week, three times/week, four times/week, five times/week, six times/week, seven times/week, once every two weeks, once every three weeks, once every four weeks, once every five weeks, and the like, can be used. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and up to twelve months or more.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The TCR T-cells according to the present disclosure may also be administered with one or more additional therapeutic agents. Methods for co-administration with an additional therapeutic agent are well known in the art (for example, Hardman, et al. (eds.) (2001) Goodman and Gilman's The Pharmacological Basis of Therapeutics, 10th ed., McGraw-Hill, New York. N.Y.; Poole and Peterson (eds.) (2001) Pharmacotherapeutics for Advanced Practice: A Practical Approach, Lippincott, Williams & Wilkins, Phila., Pa., Chabner and Longo (eds.) (2001) Cancer Chemotherapy and Biotherapy, Lippincott, Williams & Wilkins, Phila., Pa.). Examples include, but are not limited to, chemotherapeutic agents, radiation, anti-cancer agents, anti-inflammatory agents, anti-infective agents, NSAIDS, anti-pain agents, and the like. The additional therapeutic may also comprise a different TCR-T effector population. Other agents that can be part of the therapeutic regimen of the subject, such as other immunotherapy, checkpoint inhibitors, immuno-oncology drugs, targeted agents, chemotherapy, and/or radiation. Examples of agents/therapeutic regimens that may be used in combination with the compositions of the present disclosure include, but are not limited to, CTLA-4 inhibitors, PD-1 inhibitors, and/or PD-L1 inhibitors, CSF-1R inhibitors, TLR agonists, nivolumab, pembrolizumab, ipilimumab, atezolizumab, alemtuzumab, avelumab, ofatumumab, nivolumab, pembrolizumab, rituximab, durvalumab, cytokine therapy, interferons, interferon-alpha, interleukins, interleukin-2, dendritic cell therapy (e.g. Sipuleucel-T), CHOP, cyclophosphamide, fludarabine, methotrexate, 5-fluorouracil, vinorelbine, doxorubicin, docetaxel, bleomycin, dacarbazine, mustine, procarbazine, prednisolone, etoposide, cisplatin, epirubicin, folinic acid, and oxaliplatin. The T-cell population compositions of the disclosure may be administered before the additional therapeutic agent(s), concurrently with the additional therapeutic agent(s), or after the additional therapeutic agent(s).

Co-administration need not refer to administration at the same time in an individual, but rather may include administrations that are spaced by hours or even days, weeks, or longer, as long as the administration of multiple therapeutic agents is the result of a single treatment plan. The co-administration may comprise administering the TCR-T cell population of the present disclosure before, after, or at the same time as the one or more additional therapeutics. The co-administration may comprise administering a TCR T-cell population of the present disclosure before, after, or at the same time as an another TCR T-cell population. In an exemplary treatment schedule, a TCR T-cell population (e.g. A11-003) of the present disclosure may be given as an initial dose in a multi-day protocol, with another TCR T-cell population (e.g. A11-125) given on later administration days; or the TCR T-cells (e.g. A11-125) given as an initial dose in a multi-day protocol, with the TCR T-cells (e.g. A11-003) given on later administration days. On another hand, A11-003 TCR T-cells and A-125 TCR T-cells may be administered on alternate days in a multi-day protocol. This is not meant to be a limiting list of possible administration protocols.

An effective amount of a therapeutic agent is one that will decrease or ameliorate the symptoms of the cancer normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%. For example, administration of the population of T-cells comprising an engineered TCR as disclosed herein reduces tumor growth by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients treated with other cancer treatments, or the same patient before treatment.

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker. NY; Lieberman, et al. (eds.) (1990) Pharmaceutical Dosage Forms: Disperse Systems, Marcel Dekker, NY: Weiner and Kotkoskic (2000) Excipient Toxicity and Safety, Marcel Dekker, Inc., New York, N.Y.).

Methods of Making

The present disclosure provides a method preparing a population of T-cells expressing an engineered T-cell receptor (TCR) as disclosed herein, wherein the method comprises: (1) transfecting or transducing isolated T-cells with a nucleic acid encoding the engineered TCR as disclosed herein; and (2) expanding the engineered TCR-expressing T-cells following transfection or transduction, wherein the T-cells are expanded by culturing in the presence of IL-2 and/or CD3 and CD28 antibodies. In certain embodiments, the T-cells are expanded by culturing in the presence of IL-2. In certain embodiments, the T-cells are expanded by culturing in the presence of anti-CD3 antibodies. In certain embodiments, the T-cells are expanded by culturing in the presence of anti-CD28. In certain embodiments, the method of preparing the population of T-cells comprising the engineered TCR takes about 2 weeks, about 3 weeks or about 4 weeks. In certain embodiments, the method of preparing the population of T-cells comprising the engineered TCR takes less than 2 weeks, less than 3 weeks or less than 4 weeks. In certain embodiments, the T-cells are expanded by culturing in the presence of IL-2, anti-CD3 antibodies, and anti-CD28 antibodies. In certain embodiments, the isolated T-cells are isolated from a mammal. In and embodiment, the mammal is a human. In certain embodiments, the human is a subject suffering from a cancer expressing LMP2 from EBV. In an embodiment of the method, the isolated T-cells comprise HLA-A11.

Methods of introducing nucleic acids into a T-cell include physical, biological and chemical methods. Physical methods for introducing a polynucleotide, such as DNA or RNA into a host cell include calcium phosphate precipitation, lipofection, particle bombardment, microinjection, or electroporation. Nucleic acids can be introduced into target cells using commercially available methods which include electroporation, or cationic liposome mediated transfection using lipofection, or using polymer encapsulation, using peptide mediated transfection, or using biolistic particle delivery systems such as gene guns. Biological methods for introducing nucleic acids into a host cell can include the use of DNA and RNA vectors. Viral vectors, and in particular retroviral vectors, are widely used for inserting nucleic acid into human cells. Other viral vectors can be derived from lentivirus, poxviruses, herpes simplex virus I, adenoviruses and adeno-associated viruses. Examples of vectors are plasmids, autonomously replicating sequences, and transposable elements. Additional exemplary vectors can include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of animal viruses useful as vectors can include, without limitation, retrovirus (including lentivirus), adenovirus, adeno-associated virus (AAV), herpesvirus (e.g., herpes simplex virus), poxvirus, baculovirus, papillomavirus, and papovavirus (e.g., SV40). In certain embodiments, the vector comprising the TCR can be a retroviral vector.

Yet another aspect of the present disclosure provides a method of preparing a TCR-T cell-derived effector cell population comprising a population of activated T cells expressing a T cell receptor (TCR), the TCR comprising a sequence capable of activating in response to a LMP2 antigen, the method comprising, consisting of, or consisting essentially of: contacting in vitro one or more peripheral blood mononuclear cells (PBMCs) that were used to treat a patient or patients having a cancer of interest (for example, NPC); stimulating the T cells with dendritic cells expressing an antigen of interest (for example LMP2); isolating and characterizing those T cells that respond to said antigen of interest; and expanding the T cell population. In some embodiments, the method further comprises administering a therapeutically effective amount of the isolated T cell population, or a pharmaceutical composition thereof, to a patient suffering from the cancer of interest. In certain embodiments, the TCR comprises TCR-NPC-A11-003 (SEQ ID NO:3). In another embodiment, the TCR comprises TCR-NPC-A11-125 (SEQ ID NO:9). In some embodiments, the cancer of interest is characterized by the expression of LMP2. In some embodiments, the cancer is selected from the group consisting of nasopharyngeal carcinoma (NPC), gastric cancer, lung cancer, melanoma, breast cancer, prostate cancer, colon cancer, renal cell carcinoma, ovarian cancer, neuroblastoma, rhabdomyosarcoma, leukemia and lymphoma. In an embodiment, the cancer comprises NPC. In another embodiment, the cancer comprises lymphoma. In yet another embodiment, the cancer comprises gastric cancer. In certain embodiments, the cancer is an EBV-associated cancer or an EBV-positive caner, for example, EBV-positive Hodgkin's Lymphoma. EBV-positive Burkitt Lymphoma, EBV-positive nasopharyngeal carcinoma, or EBV-positive gastric cancer.

Methods of Using

The TCR-T effector cells according to the present disclosure can be used to treat subject suffering from disease, such as cancer. Accordingly, another aspect of the present disclosure provides a method of inducing a T-cell response in a subject suffering from a LMP2-characterized cancer, the method comprising, consisting of, or consisting essentially of administering to the subject a therapeutically effective amount of a TCR-T cell-derived cell population as described herein such that an anti-tumor response to the LMP2-characterized cancer is induced. Yet another aspect of the present disclosure comprises a method of treating a cancer in a subject comprising, consisting of, or consisting essentially of administering to the subject a therapeutically effective amount of a TCR-T cell-derived population as provided herein such that the cancer is treated.

Yet another aspect of the present disclosure provides all that is disclosed and illustrated herein.

The following Examples are provided by way of illustration and not by way of limitation.

EXAMPLES

Example 1. Two Novel TCR Sequences Activate in Response to LMP2 Antigen

Peripheral blood mononuclear cells (PBMCs) were obtained that were previously used to treat NPC patients and stimulated with dendritic cells presenting the EBV antigen latent membrane protein 2 (LMP2). This led to the discovery of two novel T cell receptor (TCR) sequences capable of activating in response to the LMP2 antigen (1) TCR-NPC-A11-003 (AA SEQ ID NO:03; DNA SEQ ID NO:08) (see FIGS. 1A-1B), and (2) TCR-NPC-A11-125 (AA SEQ ID NO:09; DNA SEQ ID NO:14) (see FIGS. 2A-2B).

Figure 3A:
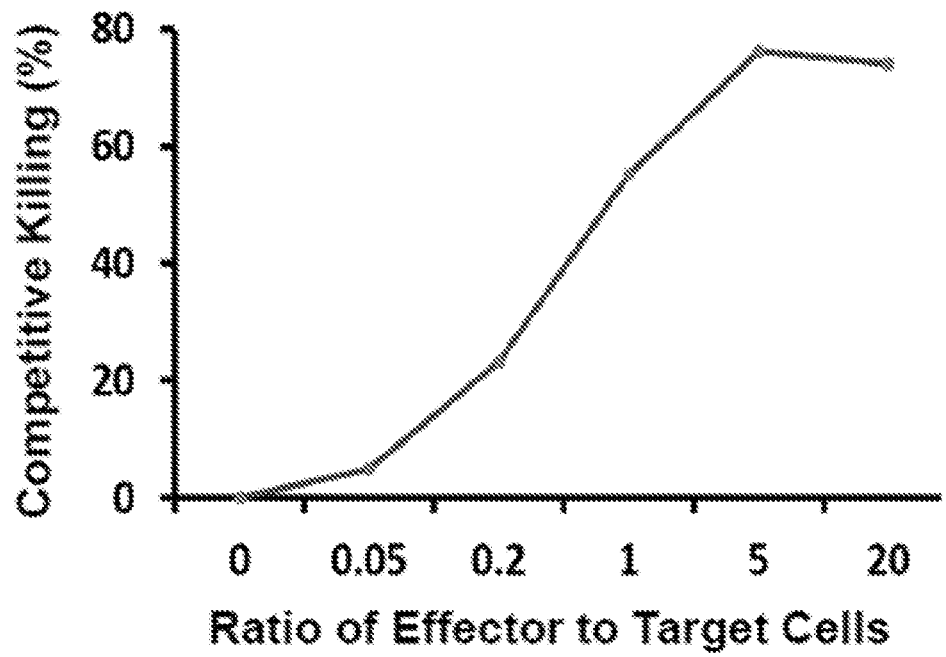
FIG. 3A-3B are graphs showing in vitro antitumor activity of LMP2-A11 TCR-T cells. PBMCs engineered to express TCR-NPC-A11-03 (A) or TCR-NPC-A11-125 (B) were co-cultured with a mixed population of Ramos cells expressing the LMP2 peptide linked to HLA-A11 or HLA-A24. The competitive killing percentage was calculated as (1-A11:A24)×100.
Figure 3B:
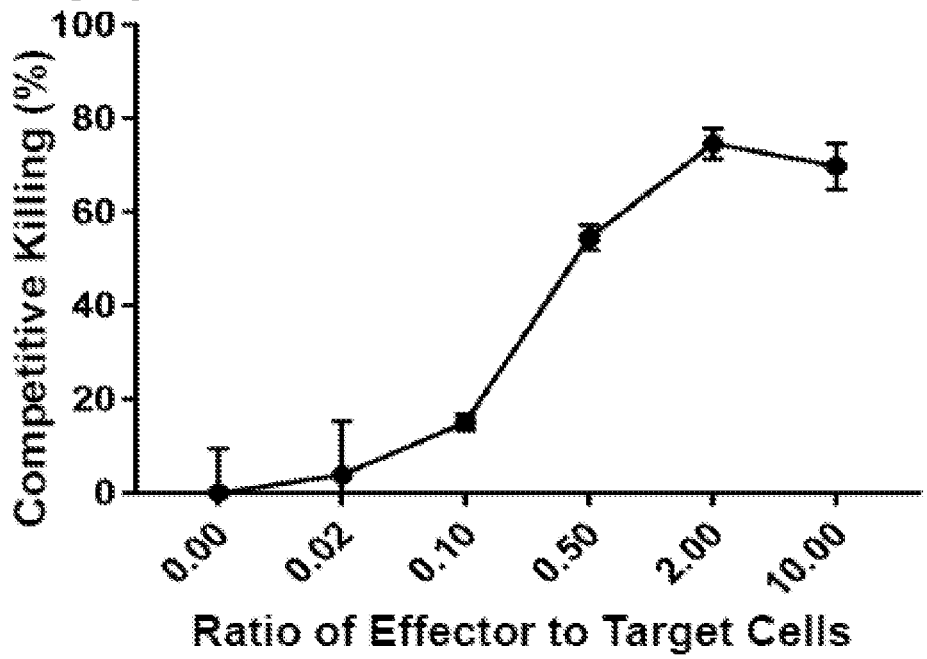

Example 2. Novel TCR Sequences TCR-NPC-A11-003 and TCR-NPC-A11-125 Kill Cells Expressing LMP2 Antigen Consistent with the CD69 activation results of Example 1, both TCR-NPC-A11-003 and TCR-NPC-A11-125 can specifically kill lymphoma cells engineered to express the LMP2 peptide linked to HLA-A11, but not HLA-A24 (see FIG. 3A-3B).

Figure 4A:
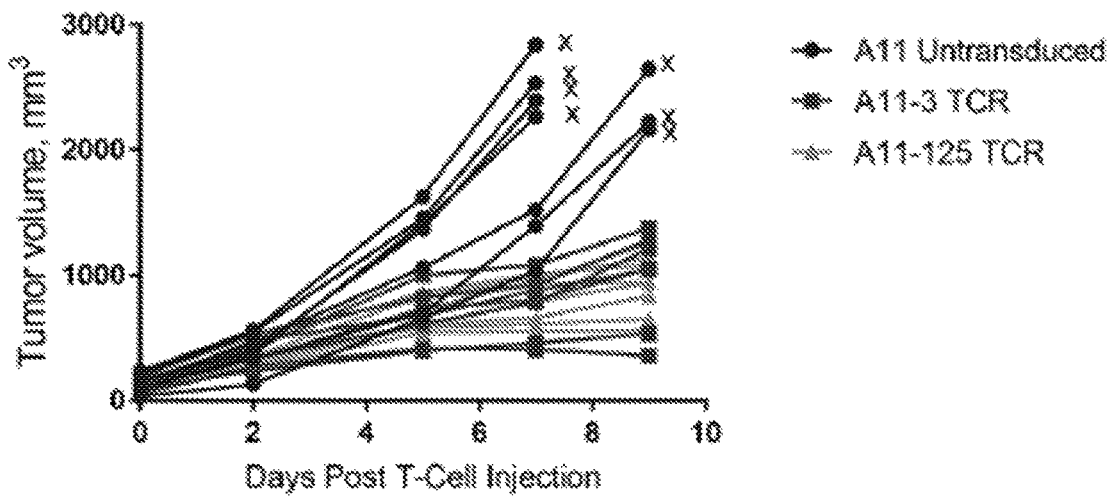
FIG. 4A-4C are graphs showing the in vivo antitumor activity of LMP2-A11 TCR-T cells. Ramos (A11) lymphoma cells ($5 \times 10^6$) were subcutaneously inoculated in NSG mice. After 13 days, $1 \times 10^7$ TCR-positive TCR-NPC-A11-03 or TCR-NPC-A11-125 TCR-T cells were injected via tail vein, as indicated. Tumor volumes were monitored and plotted individually (A) or as mean (B). Animal survival curve for each group is shown in (C).
Figure 4B:
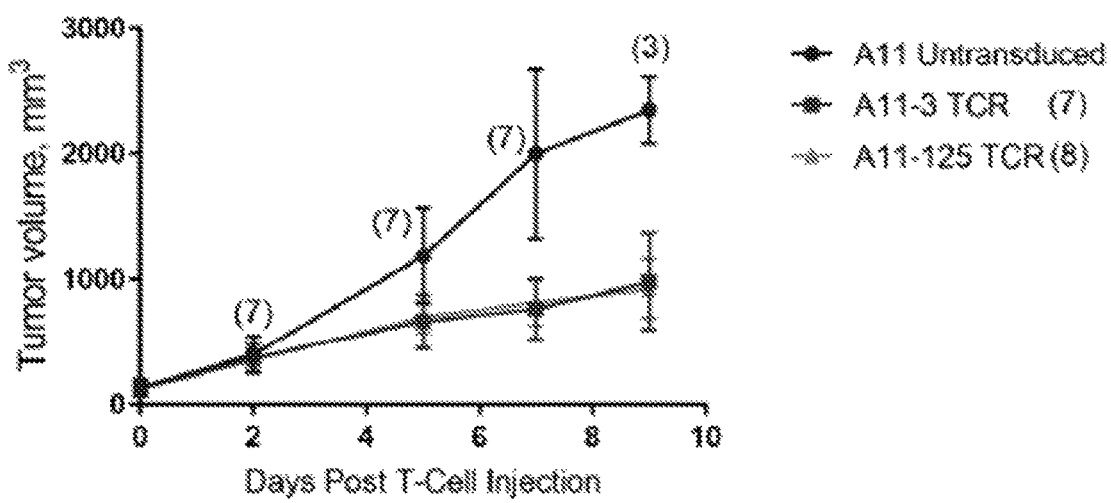
Figure 4C:
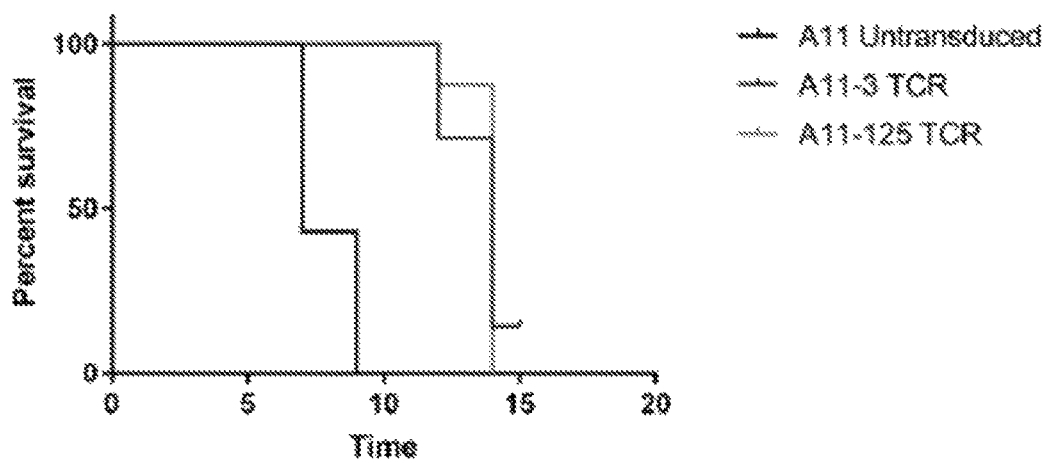

Example 3. Novel TCR Sequences TCR-NPC-A11-003 and TCR-NPC-A1-125 Have In-Vivo Antitumor Activity in Mice Mouse xenograft studies demonstrate that both TCRs have in vivo antitumor efficacy against LMP2-A11-positive lymphoma. A11-positive Ramos lymphoma cells ($5\times10^6$) were subcutaneously inoculated in NSG™ (NOD SCID gamma mouse mice). After 13 days, $1\times10^7$ TCR-positive TCR-NPC-A11-003 or TCR-NPC-A11-125 TCR-T cells were injected via tail vein. Tumor volume was significantly reduced in mice injected with TCR-NPC-A11-003 or TCR-NPC-A11-125 TCR-T cells, and these mice also had a significant increase in overall survival compared to untreated mice (see FIG. 4A-4C).

Together, these findings characterize LMP2-A11 TCR-T cells as capable of selectively killing cells harboring the LMP2 EBV viral antigen. It is important to note that both of these TCRs (TCR-NPC-A11-003 and TCR-NPC-A11-125) were identified from patient cells with the HLA-A11 serotype. HLA-A11 is particularly common in East Asia and therefore these TCRs have utility for engineered TCR-T cell therapy against EBV-associated NPC as well as lymphomas including Hodgkin and Burkitt's. This therapeutic approach also significantly lessens the time window needed to establish EBV-CTL therapies, as patient-specific TCR-T cell products can now be generated in only 3 weeks. Because no other TCR sequences capable of recognizing the LMP2 antigen presented by HLA-A11 have been previously identified, these results uncover two novel viral antigen-specific TCRs as promising agents for the treatment of at least EBV-positive NPC, gastric cancer, and lymphoma.

Figure 5:
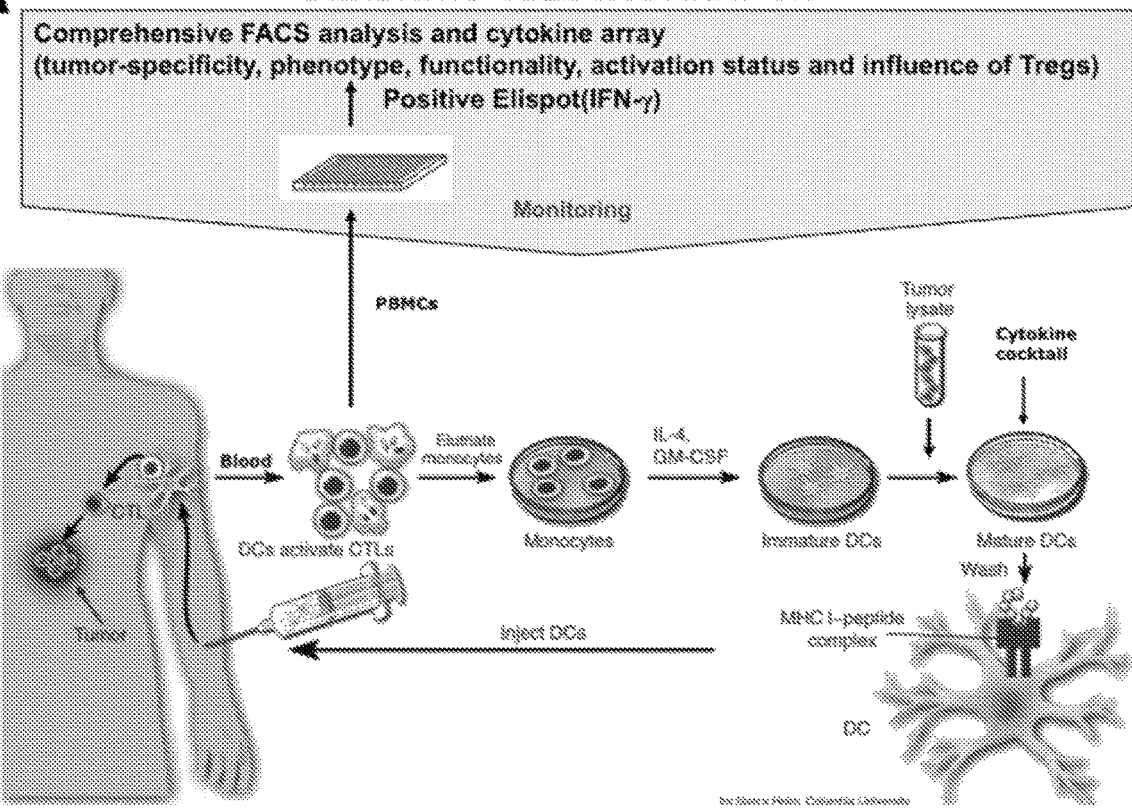
FIG. 5A-5E are graphs and schematics showing (A) and Kaplan-Meier survival analysis (B) of the first-inhuman Ad5f35-LMP1-2 adenoviral vector-transduced DC vaccine trial. Of the 16 advanced NPC patients treated. DC vaccination therapy resulted in disease stabilization for >18 weeks in two patients (12.5%) and partial response in one patient. (C-E) Schematic diagram (C), patient sample collection procedure (D), and Kaplan-Meier survival analysis of the EBV-expanded T cell therapy trial. This Phase II clinical trial for advanced NPC combining chemotherapy with adoptive EBV-specific T cell therapy achieved a response rate of 71.4%, with 3 complete and 22 partial responses in accordance with one embodiment of the present disclosure.

Example 4. Systematic T Cell Receptor Repertoire Profiling and Cloning to Improve Therapeutic Outcomes in Advanced EBV-Specific Nasopharyngeal Carcinoma Nasopharyngeal carcinoma (NPC) is highly prevalent in South China and Southeast Asia with few treatment options for late stage disease. While the current standard therapies are limited by non-specific toxicity, NPC is often associated with Epstein-Barr virus (EBV) infection, making it an excellent target for adoptive immunotherapy. For Stage IV EBV-associated NPC, a recent phase 2 clinical trial reported impressive response rates using in vitro expanded EBV-specific cytotoxic T lymphocytes (EBV-CTLs; see FIG. 5A). Although this study was successful and a phase 3 trial using the same protocol is currently underway, approximately half of the patients enrolled did not respond to the CTL treatment regimen, suggesting the involvement of unknown resistance mechanisms conferring immune evasion. Moreover, the time to generate the EBV-CTL cells used for immunotherapy ranged from 8 to 22 weeks, which is prohibitive for many patients with advanced NPC and can be significantly shortened using next-generation immune cell therapy with antigen specificity-redirected T cells.

Dendritic cell (DC) vaccination is a type of cancer immunotherapy that employs DCs' intrinsic ability to present antigen to T cells. While generally faster and cheaper in production than T cell therapy, DC vaccines have also been less reliably efficacious, although the molecular basis underlying clinical responsiveness to DC vaccination is elusive. In a 2007 clinical trial, among the 16 advanced NPC patients treated, a first-inhuman Ad5f35-LMP1-2 adenoviral vector-transduced DC vaccine led to disease stabilization for >18 weeks in two patients (12.5%) and partial response in one patient (see FIG. 5B).

T cell receptor (TCR) repertoire sequencing is performed to dissect TRC diversity in responders and non-responders, which provides additional insight into resistance mechanisms and guide the development of improved immunotherapy approaches for the treatment of NPC.

I. Identification of Molecular Determinants Underlying Response to Immunotherapy a. Discovery of MPC Prognostic Factors Via Unbiased Profiling To discover molecules governing responsiveness to EBV-specific DC vaccination, systematic cytokine/chemokine/growth factor arrays is utilized. Briefly, peripheral blood mononuclear cells (PBMCs) harvested from advanced NPC patients are sorted by flow cytometry into discreet immune cell populations including monocytes, macrophages, B cells, NK cells, and T cell subpopulations including cytotoxic, helper, memory, and regulatory T cells. After sorting, mRNA and cDNA is generated and subjected to comprehensive qPCR gene expression analysis using a panel of >100 secreted proteins. This procedure enables the identification of specific proteins regulating resistance to DC-based immunotherapy, which might be rationally targeted or otherwise exploited to improve future patient outcomes in this therapeutic context. Validation of the role of the uncovered molecules in EBV-driven cancer can be performed ex vivo and in mice using the EBV-positive lymphoma models described herein.

ii. Analyze the TCR Repertoire of Responders and Non-Responders in DC Vaccine-Treated Advanced NPC The inventors have developed a platform/system to profile the TCR repertoire within various human and mouse tissues with high reproducibility. The system comprises, consists of, or consists essentially of a multiplex PCR system that allows for the preferential read out of TCR sequences on an Illumina MiSeq platform. The system further comprises a novel bioinformatics strategy, termed "Motif Analysis", that identifies minimal structural determinants enabling antigen recognition and thereby reliably dissecting out antigen specific T cell responses from global repertoire changes during immunotherapies. This is critical to optimize the chance of TCR cloning when their targeted epitope has weak affinity or low abundance.

The inventors utilized this novel system, to assess the TCR repertoire in PBMC samples from advanced NPC patients who either responded (n=3) or did not respond (n=13) to EBV-specific DC vaccination. For this analysis, the following will be compared:
 i) global TCR diversity;
 ii) EBV-specific T cell responses; and
 iii) tumor-associated antigen (TAA) specific T cell responses longitudinally for each individual patient.

Figure 6:
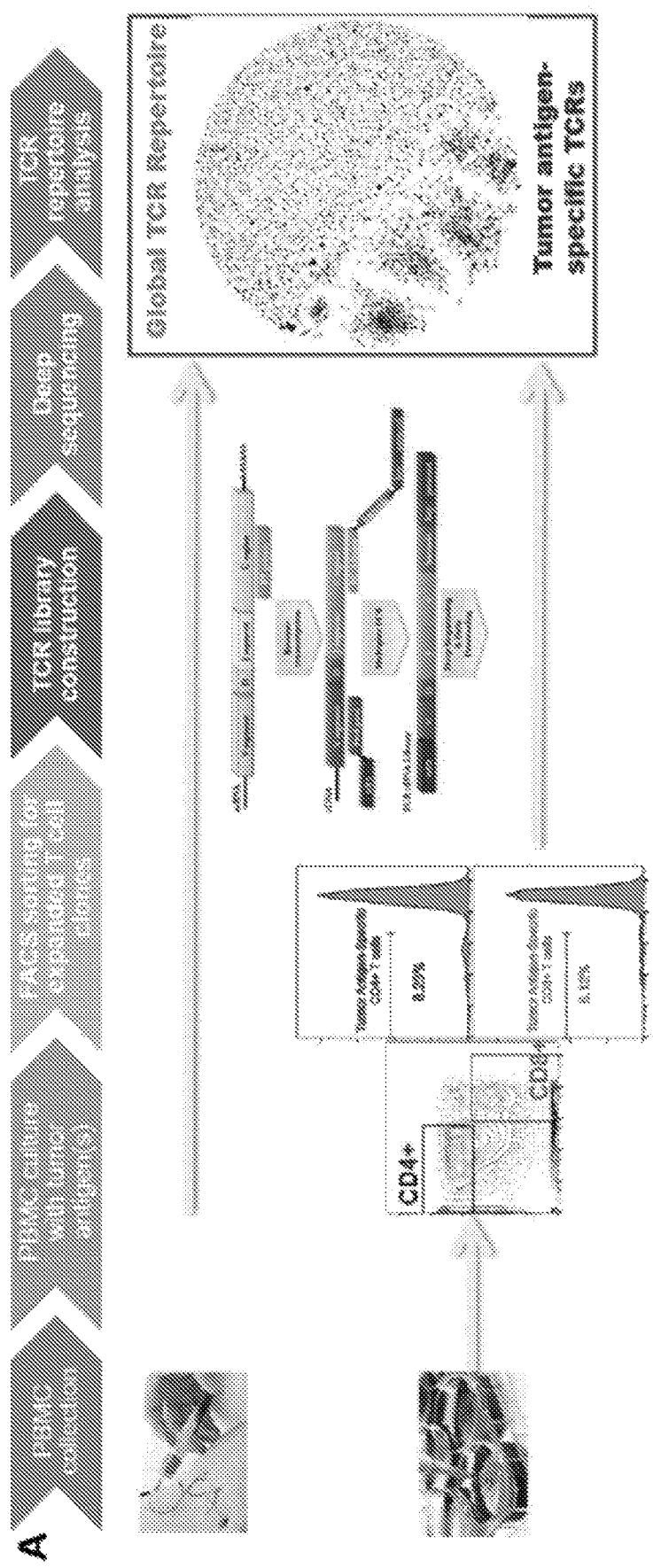
FIG. 6A-6B are graphs and images showing the experimental and computational platforms used to dissect tumor-antigen specific TCRs. (A) PBMCs from patients were aliquoted for direct repertoire sequencing or TCR analysis after tumor antigen stimulated proliferation. These two data sets were subjected to Motif analysis, which unbiasedly clusters TCRs together based on their motif similarities. In this way, even with distinct TCR sequences, TCRs recognizing the tested tumor antigen from the unstimulated pool were linked to TCRs with known tumor antigen specificity. (B) The diversity and frequency of tumor antigen-specific TCRs from a specific cluster with shared Motifs were quantified. With this procedure and longitude samples collected from the BMS CheckMate 143 Trial, we monitored the dynamics of T cell clonal expansion in glioblastoma patients treated with anti-PD-1 or anti-PD-1 plus anti-CTLA4 treatment. EGFR epitopes were used as a representative of tumor associated antigens, and CMV pp65 epitopes represented exogenous antigens.

Also, inter-patient repertoire similarity to identify dominant antigen (e.g., anti-PV clonotypes) responses is compared. Further, the method includes the following steps: i) Global TCR diversity analyses is performed as previously published, and will provide a comprehensive view of the dynamic changes of T cell clones within individual patients, ii) For EBV-specific T cell responses, LMP1-2 adenoviral vector transduced DCs is cocultured with autologous T cells. Antigen-expanded T cells are sorted for TCR repertoire sequencing to determine the breadth and strength of the anti-EBV T cell repertoire.

iii) To assess TAA-specific T cell responses, patient DCs (from PBMCs) are exposed to peptides/peptide pools representing TAAs investigated in this study (e.g. EGFR, survivin). With antigen expanded CD4+ and CD8+ TCR sequences (from ii and iii) as a training data set, TAA motifs and motif combinations can be identified. Through Jaccard similarity (distance)=analysis, a network is constructed and TCRs are assembled into clusters based on Jaccard distances calculated for each pair of TCRs (see FIG. 6). In this way, novel clonotypes (breadth) and frequency (depth) of TCRs in the original unstimulated sample (from i) are discovered. By quantifying the collective frequency of TAA-specific TCRs, treatment-elicited antitumor T cell responses are monitored.

II. Molecular Biology Platform Development—Cost-Efficient TCR Cloning Enabling a TCR-T strategy for NPC a: FBV-Specific TCR Cloning As a proof-of-principle study using single T cell RNA-Seq technology, the inventors have successfully performed high-throughput cloning of cytomegalovirus (CMV)-specific TCRs. These TCRs were expressed in PBMCs through retroviral transduction, and their specificity and cytotoxicity was validated in vitro (see FIG. 7). Using the same technology, the inventors assembled a small library (up to 20) of TCR-expressing viruses and employ the TCR production procedure described herein to generate EBV-specific TCR-T cells. Since EBV-positive NPC cell lines have not been established, EBV-positive lymphoma cells are used to assess the killing capacity of TCR-T cells. Each TCR-T cell line is tested in vitro for its specificity to kill the EBV-positive Raji lymphoma cells but not EBV-negative Ramos cells. Any TCR that fails this functional test is replaced with a new one with similar characteristics as identified by RNA-Seq.

b: Establish the Safety of TCR-T Cell Therapy in Mice Bearing EBV-Positive Lymphoma MHC-humanized mice are treated with a mixed TCR-T population consisting of 5 CD4+ and 5 CD8+ TCRs against the EBV epitope. In this design, rapid EBV specific T-cell expansion and cytolytic activity against tumors using CD8+ T cells are delivered; and CD4+ T cells are utilized to enforce efficient CD8+ memory T-cell differentiation to achieve long-term protection. The clinical value of this strategy is formally examined for its toxicity and efficacy. To exclude potential toxicities, animal toxicity assays are conducted. In accordance with FDA guidelines, acute and chronic toxicity studies are performed at 3 dose levels for assessment of histopathologic toxicity, carcinogenicity, dermal toxicity, and neurotoxicity in a single rodent species. Acute studies comprise intravenous (IV) infusion followed by a 2-week observation period. Chronic studies consist of IV infusion followed by a 6-month observation period. Dose levels translate to doses that are similar to perfusion procedures in human trials, which allows for direct translation into future human studies. Whole blood counts, chemistries, enzymes, and autoimmune serology are monitored weekly, and mice are assessed daily by weight and neurological examination. Mice are autopsied at death or when they show defined signs of toxicity or neurological deficit. The safety of EBV TCR-T cells is monitored in all experiments outlined below as well using the same clinical, chemical, immunological, histopathological, and statistical evaluations.

c: Establish the Efficacy of TCR-T Cell Therapy in Mice Bearing EBV-Positive Lymphoma The efficacy of the generated EBV TCR-T strategy is evaluated using a tumor xenograft model in NOD/SCID mice. $1\times10^6$ EBV+Raji cells are subcutaneously transplanted, and tumor sizes are measured daily. Three weeks after inoculation, EBV TCR-T cells (CD4+ TCR-T cells, CD8+ TCR-T cells, or the combination) are intravenously infused into tumor-bearing mice. Mice with established tumor display prolonged survival after IV delivery of the MTD or the maximum feasible dose of $2\times10^7$ EBV-specific TCR-T cells are assessed. Two additional tumor-bearing cohorts will receive dose-matched T cells with control GFP-transduced T cells or tumor alone. Success in treating these tumors with EBV-specific TCR-T guides the development of future clinical trials for EBV-positive cancers based on the same TCR cloning principles.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

We claim:

1. A population of T-cells comprising an engineered T-cell receptor (TCR), wherein the engineered TCR activates T-cells in response to a Latent membrane protein 2 (LMP2) antigen; and wherein the engineered TCR comprises a variable alpha chain comprising the sequence as set forth in SEQ ID NO:4, and a variable beta chain comprising the amino acid sequence as set forth in SEQ ID NO:6; or a variable alpha chain comprising the sequence set forth in SEQ ID NO:10 and a variable beta chain comprising the sequence set forth in SEQ ID NO: 12.

2. The population of T-cells of claim 1, wherein the engineered TCR comprises the amino acid sequence as set forth in SEQ ID NO:3.

3. The population of T-cells of claim 1, wherein the engineered TCR comprises the amino acid sequence as set forth in SEQ ID NO:9.

4. The population of T-cells of claim 1, wherein the population of T-cells comprises a therapeutically effective amount of cells for the treatment of a cancer comprising LMP2 in a subject.

5. The population of T-cells of claim 4, wherein the subject expresses human leukocyte antigen subtype A11 (HLA-A11).

6. The population of T-cells of claim 1, wherein at least a portion of the population of T-cells produces or has the potential to produce one or more cytokines.

7. The population of T-cells of claim 6, wherein the one or more cytokines are selected from the group consisting of IL-2, IFN-gamma, TNF-alpha, Granzyme A, Granzyme B, and GM-CSF.

8. The population of T-cells of claim 4, wherein the cancer is selected from the group consisting of nasopharyngeal carcinoma (NPC), lymphoma, gastric cancer, lung cancer, melanoma, breast cancer, prostate cancer, colon cancer, renal cell carcinoma, ovarian cancer, neuroblastoma, rhabdomyosarcoma, and leukemia.

9. The population of T-cells of claim 8, wherein the cancer is an EBV-associated cancer.

10. The population of T-cells of claim 9, wherein the cancer is EBV-positive nasopharyngeal carcinoma (NPC), EBV-positive lymphoma, or EBV-positive gastric cancer.

11. A pharmaceutical composition, wherein the composition comprises the population of T-cells of claim 1, and a pharmaceutically acceptable carrier.

12. The pharmaceutical composition of claim 11, wherein the pharmaceutically acceptable carrier supports maintenance of a therapeutically effective amount of cells for the treatment of a cancer comprising LMP2.

13. The pharmaceutical composition of claim 11, further comprising at least one therapeutic agent.

14. A method of treating a subject suffering from a cancer comprising LMP2, said method comprising administering to the subject a therapeutically effective amount of the population of T-cells of claim 1.

15. The method of claim 14, wherein the cancer is selected from group consisting of nasopharyngeal carcinoma (NPC), lymphoma, gastric cancer, lung cancer, melanoma, breast cancer, prostate cancer, colon cancer, renal cell carcinoma, ovarian cancer, neuroblastoma, rhabdomyosarcoma, and leukemia.

16. The method of claim 15, wherein the cancer is an EBV-associated cancer.

17. The method of claim 16, wherein the cancer is EBV-positive nasopharyngeal carcinoma (NPC), EBV-positive lymphoma, or EBV-positive gastric cancer.

18. A method of inhibiting the growth of a tumor comprising LMP2 in a subject in need thereof, said method comprising administering to the subject a therapeutically effective amount of the population of T-cells of claim 1.

19. A method of inducing a T-cell response in a subject suffering from a cancer comprising LMP2, said method comprising administering to the subject a therapeutically effective amount of the population of T-cells of claim 1.

* * * * *

SEQUENCE LISTING

```
<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: LMP2 antigen

<400> SEQUENCE: 1

Ser Ser Cys Ser Ser Cys Pro Leu Ser Lys
1               5                   10

<210> SEQ ID NO 2
<211> LENGTH: 497
<212> TYPE: PRT
<213> ORGANISM: Human herpesvirus 4

<400> SEQUENCE: 2

Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
        115                 120                 125

Val Ala Pro Tyr Leu Phe Trp Leu Ala Ala Ile Ala Ala Ser Cys Phe
    130                 135                 140
```

```
Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
            165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
        195                 200                 205

Leu Phe Ala Leu Leu Ala Ala Gly Gly Leu Gln Gly Ile Tyr Val
    210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
                260                 265                 270

Thr Val Val Ser Met Thr Leu Leu Leu Ala Phe Val Leu Trp Leu
            275                 280                 285

Ser Ser Pro Gly Gly Leu Gly Thr Leu Gly Ala Ala Leu Leu Thr Leu
290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
                325                 330                 335

Leu Ile Cys Ser Ser Cys Ser Cys Pro Leu Ser Lys Ile Leu Leu
        340                 345                 350

Ala Arg Leu Phe Leu Tyr Ala Leu Ala Leu Leu Leu Ala Ser Ala
            355                 360                 365

Leu Ile Ala Gly Gly Ser Ile Leu Gln Thr Asn Phe Lys Ser Leu Ser
    370                 375                 380

Ser Thr Glu Phe Ile Pro Asn Leu Phe Cys Met Leu Leu Leu Ile Val
385                 390                 395                 400

Ala Gly Ile Leu Phe Ile Leu Ala Ile Leu Thr Glu Trp Gly Ser Gly
                405                 410                 415

Asn Arg Thr Tyr Gly Pro Val Phe Met Cys Leu Gly Gly Leu Leu Thr
            420                 425                 430

Met Val Ala Gly Ala Val Trp Leu Thr Val Met Ser Asn Thr Leu Leu
            435                 440                 445

Ser Ala Trp Ile Leu Thr Ala Gly Phe Leu Ile Phe Leu Ile Gly Phe
        450                 455                 460

Ala Leu Phe Gly Val Ile Arg Cys Cys Arg Tyr Cys Cys Tyr Cys
465                 470                 475                 480

Leu Thr Leu Glu Ser Glu Glu Arg Pro Pro Thr Pro Tyr Arg Asn Thr
                485                 490                 495

Val

<210> SEQ ID NO 3
<211> LENGTH: 421
<212> TYPE: PRT
<213> ORGANISM: Artificial Sequence
<220> FEATURE:
<223> OTHER INFORMATION: TCR A11-003

<400> SEQUENCE: 3

Met Lys Arg Ile Leu Gly Ala Leu Leu Gly Leu Leu Ser Ala Gln Val
```

-continued

```
  1               5                   10                  15
Cys Cys Val Arg Gly Ile Gln Val Glu Gln Ser Pro Pro Asp Leu Ile
             20                  25                  30

Leu Gln Glu Gly Ala Asn Ser Thr Leu Arg Cys Asn Phe Ser Asp Ser
             35                  40                  45

Val Asn Asn Leu Gln Trp Phe His Gln Asn Pro Trp Gly Gln Leu Ile
 50                  55                  60

Asn Leu Phe Tyr Ile Pro Ser Gly Thr Lys Gln Asn Gly Arg Leu Ser
 65                  70                  75                  80

Ala Thr Thr Val Ala Thr Glu Arg Tyr Ser Leu Leu Tyr Ile Ser Ser
             85                  90                  95

Ser Gln Thr Thr Asp Ser Gly Val Tyr Phe Cys Ala Val Val Asn Asn
            100                 105                 110

Asn Asp Met Arg Phe Gly Ala Gly Thr Arg Leu Thr Val Lys Pro Asp
            115                 120                 125

Ile Gln Asn Pro Glu Pro Ala Val Tyr Gln Leu Lys Asp Pro Arg Ser
130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Thr Val
            165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
            195                 200                 205

Ala Cys Tyr Pro Ser Ser Asp Val Pro Cys Asp Ala Thr Leu Thr Glu
210                 215                 220

Lys Ser Phe Glu Thr Asp Met Asn Leu Asn Phe Gln Asn Leu Ser Val
225                 230                 235                 240

Met Gly Leu Arg Ile Leu Leu Leu Lys Val Ala Gly Phe Asn Leu Leu
            245                 250                 255

Met Thr Leu Arg Leu Trp Ser Ser Arg Ala Lys Arg Gly Ser Gly Ala
            260                 265                 270

Thr Asn Phe Ser Leu Leu Lys Gln Ala Gly Asp Val Glu Glu Asn Pro
            275                 280                 285

Gly Pro Met Gly Cys Arg Leu Leu Cys Cys Ala Val Leu Cys Leu Leu
            290                 295                 300

Gly Ala Val Pro Ile Asp Thr Glu Val Thr Gln Thr Pro Lys His Leu
305                 310                 315                 320

Val Met Gly Met Thr Asn Lys Lys Ser Leu Lys Cys Glu Gln His Met
            325                 330                 335

Gly His Arg Ala Met Tyr Trp Tyr Lys Gln Lys Ala Lys Lys Pro Pro
            340                 345                 350

Glu Leu Met Phe Val Tyr Ser Tyr Glu Lys Leu Ser Ile Asn Glu Ser
            355                 360                 365

Val Pro Ser Arg Phe Ser Pro Glu Cys Pro Asn Ser Ser Leu Leu Asn
            370                 375                 380

Leu His Leu His Ala Leu Gln Pro Glu Asp Ser Ala Leu Tyr Leu Cys
385                 390                 395                 400

Ala Ser Ser Pro Gly Arg Trp Tyr Glu Gln Phe Phe Gly Pro Gly Thr
            405                 410                 415

Arg Leu Thr Val Leu
            420
```

<210> SEQ ID NO 4
<211> LENGTH: 127
<212> TYPE: PRT
<213> ORGANISM: Artificial Sequence
<220> FEATURE:
<223> OTHER INFORMATION: TCR A11-003 Variable alpha chain

<400> SEQUENCE: 4

```
Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Val Asn Asn
            100                 105                 110

Asn Asp Met Arg Phe Gly Ala Gly Thr Arg Leu Thr Val Lys Pro
        115                 120                 125
```

<210> SEQ ID NO 5
<211> LENGTH: 11
<212> TYPE: PRT
<213> ORGANISM: Artificial Sequence
<220> FEATURE:
<223> OTHER INFORMATION: TCR A11-003 Variable CDR3 alpha

<400> SEQUENCE: 5

```
Ala Val Val Asn Asn Asn Asp Met Arg Phe Gly
1               5                   10
```

<210> SEQ ID NO 6
<211> LENGTH: 131
<212> TYPE: PRT
<213> ORGANISM: Artificial Sequence
<220> FEATURE:
<223> OTHER INFORMATION: TCR A11-003 Variable beta chain

<400> SEQUENCE: 6

```
Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110
```

```
Ser Pro Gly Arg Trp Tyr Glu Gln Phe Phe Gly Pro Gly Thr Arg Leu
        115                 120                 125

Thr Val Leu
    130

<210> SEQ ID NO 7
<211> LENGTH: 11
<212> TYPE: PRT
<213> ORGANISM: Artificial Sequence
<220> FEATURE:
<223> OTHER INFORMATION: TCR A11-003 Variable CDR3 beta

<400> SEQUENCE: 7

Ala Ser Ser Pro Gly Arg Trp Tyr Glu Gln Phe
1               5                   10

<210> SEQ ID NO 8
<211> LENGTH: 1263
<212> TYPE: DNA
<213> ORGANISM: Artificial Sequence
<220> FEATURE:
<223> OTHER INFORMATION: TCR A11-003

<400> SEQUENCE: 8
atgaagagaa tcctgggcgc tctgctggga ctgctgtctg ctcaagtgtg ctgtgtgcgg     60
ggcatccagg tggaacaaag ccctcctgac ctgatcctgc aagagggcgc caatagcacc    120
ctgcggtgca actttagcga cagcgtgaac aacctgcagt ggttccacca gaatccttgg    180
ggccagctga tcaacctgtt ctacatcccc agcggcacca agcagaacgg cagactgtct    240
gctaccaccg tggccaccga gagatacagc ctgctgtaca tcagcagcag ccagaccaca    300
gacagcggcg tgtacttttg cgccgtggtc aacaacaacg acatgagatt cggagccggc    360
accagactga ccgtgaagcc cgatatccag aatccagagc tgccgtgta ccagctgaag    420 gaccctagaa gccaggacag caccctgtgc ctgttcaccg acttcgacag ccagatcaac    480
gtgcccaaga ccatggaaag cggcaccttc atcaccgaca gaccgtgct ggacatgaag    540 gccatggaca gcaagagcaa cggcgccatt gcctggtcca accagaccag cttcacatgc    600
caggacatct tcaaagagac aaacgcctgc tatcccagca gcgacgtgcc ctgtgatgcc    660
acactgaccg agaagtcctt cgagacagag atgaacctga acttccagaa cctgagcgtg    720
atgggcctgc gcatcctgct gcttaaagtg gccggcttca acctgctgat gaccctgaga    780
ctgtggtcca gcagggccaa gagaggaagc ggcgccacaa actttagcct gctgaaacag    840
gccggcgacg tggaagaaaa ccctggacct atgggctgca gactgctgtg ttgtgccgtg    900
ctgtgtctgc tgggcgccgt gcctattgac accgaagtga cccagacacc taagcacctg    960
gtcatgggca tgacaaacaa gaaaagcctg aagtgcgagc agcacatggg ccacagagcc   1020
atgtactggt acaagcagaa ggccaagaaa cctccagagc tgatgttcgt gtacagctac   1080
gagaagctga gcatcaacga gagcgtgccc agcaggttca gccctgagtg tcctaatagc   1140
tccctgctga atctgcatct gcacgccctg cagcctgagg attctgccct gtacctgtgt   1200
gccagctctc ccggacgttg gtacgagcag ttttttcggcc ctggcacacg gctgacagtt   1260
ctg                                                                 1263

<210> SEQ ID NO 9
<211> LENGTH: 421
<212> TYPE: PRT
<213> ORGANISM: Artificial Sequence
<220> FEATURE:
```

<223> OTHER INFORMATION: TCR A11-125

<400> SEQUENCE: 9

```
Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Leu Asn Asn
            100                 105                 110

Asn Asp Met Arg Phe Gly Ala Gly Thr Arg Leu Thr Val Lys Pro Asp
        115                 120                 125

Ile Gln Asn Pro Glu Pro Ala Val Tyr Gln Leu Lys Asp Pro Arg Ser
    130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Thr Val
                165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
        195                 200                 205

Ala Cys Tyr Pro Ser Ser Asp Val Pro Cys Asp Ala Thr Leu Thr Glu
    210                 215                 220

Lys Ser Phe Glu Thr Asp Met Asn Leu Asn Phe Gln Asn Leu Ser Val
225                 230                 235                 240

Met Gly Leu Arg Ile Leu Leu Leu Lys Val Ala Gly Phe Asn Leu Leu
                245                 250                 255

Met Thr Leu Arg Leu Trp Ser Ser Arg Ala Lys Arg Gly Ser Gly Ala
            260                 265                 270

Thr Asn Phe Ser Leu Leu Lys Gln Ala Gly Asp Val Glu Glu Asn Pro
        275                 280                 285

Gly Pro Met Gly Cys Arg Leu Leu Cys Cys Ala Val Leu Cys Leu Leu
    290                 295                 300

Gly Ala Val Pro Ile Asp Thr Glu Val Thr Gln Thr Pro Lys His Leu
305                 310                 315                 320

Val Met Gly Met Thr Asn Lys Lys Ser Leu Lys Cys Glu Gln His Met
                325                 330                 335

Gly His Arg Ala Met Tyr Trp Tyr Lys Gln Lys Ala Lys Lys Pro Pro
            340                 345                 350

Glu Leu Met Phe Val Tyr Ser Tyr Glu Lys Leu Ser Ile Asn Glu Ser
        355                 360                 365

Val Pro Ser Arg Phe Ser Pro Glu Cys Pro Asn Ser Ser Leu Leu Asn
    370                 375                 380

Leu His Leu His Ala Leu Gln Pro Glu Asp Ser Ala Leu Tyr Leu Cys
385                 390                 395                 400
```

```
Ala Ser Ser Gln Gly Arg Trp Tyr Glu Ala Phe Phe Gly Gln Gly Thr
                405                 410                 415

Arg Leu Thr Val Val
        420

<210> SEQ ID NO 10
<211> LENGTH: 127
<212> TYPE: PRT
<213> ORGANISM: Artificial Sequence
<220> FEATURE:
<223> OTHER INFORMATION: TCR A11-125 Variable alpha chain

<400> SEQUENCE: 10

Met Lys Arg Ile Leu Gly Ala Leu Leu Gly Leu Leu Ser Ala Gln Val
 1                5                  10                  15

Cys Cys Val Arg Gly Ile Gln Val Glu Gln Ser Pro Pro Asp Leu Ile
                20                  25                  30

Leu Gln Glu Gly Ala Asn Ser Thr Leu Arg Cys Asn Phe Ser Asp Ser
            35                  40                  45

Val Asn Asn Leu Gln Trp Phe His Gln Asn Pro Trp Gly Gln Leu Ile
 50                  55                  60

Asn Leu Phe Tyr Ile Pro Ser Gly Thr Lys Gln Asn Gly Arg Leu Ser
 65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Leu Asn Asn
            100                 105                 110

Asn Asp Met Arg Phe Gly Ala Gly Thr Arg Leu Thr Val Lys Pro
        115                 120                 125

<210> SEQ ID NO 11
<211> LENGTH: 11
<212> TYPE: PRT
<213> ORGANISM: Artificial Sequence
<220> FEATURE:
<223> OTHER INFORMATION: TCR A11-125 Variable CDR3 alpha

<400> SEQUENCE: 11

Ala Val Leu Asn Asn Asn Asp Met Arg Phe Gly
 1                5                  10

<210> SEQ ID NO 12
<211> LENGTH: 131
<212> TYPE: PRT
<213> ORGANISM: Artificial Sequence
<220> FEATURE:
<223> OTHER INFORMATION: TCR A11-125 Variable beta chain

<400> SEQUENCE: 12

Met Gly Cys Arg Leu Leu Cys Cys Ala Val Leu Cys Leu Leu Gly Ala
 1                5                  10                  15

Val Pro Ile Asp Thr Glu Val Thr Gln Thr Pro Lys His Leu Val Met
                20                  25                  30

Gly Met Thr Asn Lys Lys Ser Leu Lys Cys Glu Gln His Met Gly His
            35                  40                  45

Arg Ala Met Tyr Trp Tyr Lys Gln Lys Ala Lys Lys Pro Pro Glu Leu
        50                  55                  60

Met Phe Val Tyr Ser Tyr Glu Lys Leu Ser Ile Asn Glu Ser Val Pro
 65                  70                  75                  80

Ser Arg Phe Ser Pro Glu Cys Pro Asn Ser Ser Leu Leu Asn Leu His
```

```
                  85                  90                  95
Leu His Ala Leu Gln Pro Glu Asp Ser Ala Leu Tyr Leu Cys Ala Ser
             100                 105                 110

Ser Gln Gly Arg Trp Tyr Glu Ala Phe Phe Gly Gln Gly Thr Arg Leu
         115                 120                 125

Thr Val Val
    130

<210> SEQ ID NO 13
<211> LENGTH: 11
<212> TYPE: PRT
<213> ORGANISM: Artificial Sequence
<220> FEATURE:
<223> OTHER INFORMATION: TCR A11-125 Variable CDR3 beta

<400> SEQUENCE: 13

Ala Ser Ser Gln Gly Arg Trp Tyr Glu Ala Phe
1               5                   10

<210> SEQ ID NO 14
<211> LENGTH: 1263
<212> TYPE: DNA
<213> ORGANISM: Artificial Sequence
<220> FEATURE:
<223> OTHER INFORMATION: TCR A11-125

<400> SEQUENCE: 14
atgaagagaa tcctgggcgc tctgctggga ctgctgtctg ctcaagtgtg ctgtgtgcgg      60
ggcatccagg tgaacagtc tccaccagac ctgatcctgc aagagggcgc caatagcacc     120
ctgcggtgca actttagcga cagcgtgaac aacctgcagt ggttccacca gaatccttgg     180
ggccagctga tcaacctgtt ctacatcccc agcggcacca gcagaacgg cagactgtct     240 gctaccaccg tggccaccga gatacagc ctgctgtaca tcagcagcag ccagaccaca     300
gacagcggcg tgtacttttg cgccgtgctg aacaacaacg acatgagatt cggagccggc     360
accagactga ccgtgaagcc cgatatccag aatccagagc tgccgtgta ccagctgaag     420 gacccctaga aggcaggacag caccctgtgc ctgttcaccg acttcgacag ccagatcaac     480
gtgcccaaga ccatggaaag cggcaccttc atcaccgaca gaccgtgct ggacatgaag     540 gccatggaca gcaagagcaa cggcgccatt gcctggtcca accagaccag cttcacatgc     600
caggacatct tcaaagagac aaacgcctgc tatcccagca gcgacgtgcc ctgtgatgcc     660
acactgaccg agaagtcctt cgagacagac atgaacctga acttccagaa cctgagcgtg     720
atgggcctgc gcatcctgct gcttaaagtg gccggcttca acctgctgat gaccctgaga     780
ctgtggtcca gcagggccaa gagaggaagc ggcgccacaa actttagcct gctgaaacag     840
gccggcgacg tggaagaaaa ccctggacct atgggctgca gactgctgtg ttgtgccgtg     900
ctgtgtctgc tgggcgccgt gcctattgac accgaagtga cccagacacc taagcacctg     960
gtcatgggca tgacaaacaa gaaaagcctg aagtgcgagc agcacatggg ccacagagcc    1020
atgtactggt acaagcagaa ggccaagaaa cctcctgagc tgatgttcgt gtacagctac    1080
gagaagctga gcatcaacga gagcgtgccc agcaggttca gccctgagtg tcctaatagc    1140
tccctgctga atctgcatct gcacgccctg cagcctgagg attctgccct gtatctgtgc    1200
gccagctctc aaggacgttg gtacgaggcc ttcttcggcc aaggcacaag gctgacagtg    1260
gtg                                                                  1263
```